US012742211B2

(12) United States Patent
Cote et al.

(10) Patent No.: US 12,742,211 B2
(45) Date of Patent: Sep. 22, 2026

(54) BUFFER COMPOSITIONS FOR REDUCING AGGREGATION

(71) Applicant: Becton, Dickinson and Company, Franklin Lakes, NJ (US)

(72) Inventors: Jean-Sebastien Cote, Levis (CA); Marie-Christine Fortin, Québec (CA); Vincent Blanchette, Québec (CA); Marie-Helene Tremblay, Québec (CA); Sebastien Morasse, Québec (CA); Sophie Guay, Beaumont (CA); Sebastien Simard, Québec (CA)

(73) Assignee: Augusta SpinCo Corporation, Milford, MA (US)

( * ) Notice: Subject to any disclaimer, the term of this patent is extended or adjusted under 35 U.S.C. 154(b) by 1157 days.

(21) Appl. No.: 17/584,266

(22) Filed: Jan. 25, 2022

(65) Prior Publication Data

US 2022/0145373 A1 May 12, 2022

Related U.S. Application Data

(63) Continuation of application No. PCT/US2020/043093, filed on Jul. 22, 2020.

(60) Provisional application No. 62/879,310, filed on Jul. 26, 2019.

(51) Int. Cl.
*C12Q 1/689* (2018.01)
*C12Q 1/6806* (2018.01)

(52) U.S. Cl.
CPC ........... *C12Q 1/689* (2013.01); *C12Q 1/6806* (2013.01)

(58) Field of Classification Search
None
See application file for complete search history.

(56) References Cited

U.S. PATENT DOCUMENTS

| | | | | |
|---|---|---|---|---|
| 10,047,406 | B2* | 8/2018 | Gao | C12Q 1/707 |
| 2004/0180444 | A1* | 9/2004 | Rannikko | G01N 21/8483 436/15 |
| 2008/0038782 | A1 | 2/2008 | Borns | |
| 2008/0124728 | A1 | 5/2008 | Baker | |
| 2011/0262893 | A1 | 10/2011 | Dryga et al. | |
| 2013/0130253 | A1 | 5/2013 | Hilbert et al. | |
| 2014/0186821 | A1* | 7/2014 | Daum | C12Q 1/6806 435/6.12 |
| 2015/0210989 | A1 | 7/2015 | Rogers et al. | |
| 2015/0211047 | A1* | 7/2015 | Borns | C12Q 1/6806 435/6.11 |
| 2019/0390249 | A1* | 12/2019 | Fischer | C12Q 1/6806 |

FOREIGN PATENT DOCUMENTS

| | | | |
|---|---|---|---|
| EP | 3135769 | A1 | 3/2017 |
| RU | 2651937 | C1 | 4/2018 |
| WO | WO 2003/070898 | A2 | 8/2003 |
| WO | WO 2004/024919 | A1 | 3/2004 |

OTHER PUBLICATIONS

Farsang, E. et al., "Analysis of non-ionic surfactant Triton X-100 using hydrophilic interaction liquid chromatography and mass spectrometry," Molecules, vol. 24, pp. 1-13, Mar. 28, 2019.*
International Search Report and Written Opinion dated Oct. 16, 2020 for Application No. PCT/US2020/043093.
Aguirre-Quiñonero et al., Accuracy of the BD MAX™ Vaginal Panel in the Diagnosis of Infectious Vaginitis. Euro J Clin Microbiol Inf Dis. Jan. 26, 2019;38(5): 877-882.
McNeill et al., Surfactant Protein A, an Innate Immune Factor, is Expressed in the Vaginal Mucosa and is Present in Vaginal Lavage Fluid. Immunol. Jan. 2004; 111(1): 91-99.
Nacalai-Tesque. Reducing Agent to Cleave Disulfide Bond, TCEP-HCl, Sep. 2016; downloaded from URL: https://www.nacalai.co.jp/products/entry/d004010.html. in 9 pages.
Wikipedia "Isothiazolinone", [online], Oct. 22, 2018, downloaded from URL: http://web.archive.org/web/20181022120929/https://ja.wikipedia.org/wiki/%E3%82%A4%E3%82%BD%E3%83%81%E3%82%A2%E3%82%BE%E3%83%AA%E3%83%8E%E3%83%B3 in 1 page.
European Extended Search Report dated Jun. 26, 2023 for Application No. 20847041.9 in 12 pages.

* cited by examiner

*Primary Examiner* — John Pak
(74) *Attorney, Agent, or Firm* — Knobbe, Martens, Olson & Bear, LLP

(57) ABSTRACT

Disclosed include compositions, kits and methods for nucleic acid-based detection and identification of vaginal disorders, for example, vulvovaginal candidiasis, trichomoniasis and/or bacterial vaginosis. The compositions, kits and methods can be used for obtaining robust diagnostic testing performance against interfering substances, for example, gels present in clinical vaginal-swab samples.

18 Claims, 6 Drawing Sheets

$A_I$
$A_{II}$
$A_{III}$
$B_I$
$B_{II}$
$B_{III}$

A_I
A_II
A_III
B_I
B_II
B_III

Comparative Buffer + Routine Workflow
Comparative Buffer + Optimized Workflow
Example Buffer + Optimized Workflow Cy5.5 EP
6000
4500
3000
1500
0
137
30
35
40
Cy5.5 Ct Score 10
40
7500
5000
2500
15
45
Cy5.5 SDPA Comparative Buffer + Routine Workflow
Comparative Buffer + Optimized Workflow
Example Buffer + Optimized Workflow Cy5.5 EP
3000
2000
1000
0
Cy5.5 Ct Score
30
36
42
236
Cy5.5 SDPA
15
24.5
30
33.4
45

BUFFER COMPOSITIONS FOR REDUCING AGGREGATION

CROSS-REFERENCE TO RELATED APPLICATIONS

This application is a continuation of International Patent Application No. PCT/US2020/043093, filed on Jul. 22, 2020, which claims priority to the U.S. Provisional Patent Application Ser. No. 62/879,310, filed on Jul. 26, 2019, which is hereby incorporated by reference herein in its entirety.

BACKGROUND

Technical Field

The present disclosure relates to compositions, kits and methods, including for example, buffer compositions, assay kits comprising thereof, their uses and methods of diagnostic testing for vaginal disorders or/and sexually transmitted diseases therewith. In some embodiments, the compositions, kits and methods achieve robust high-performance diagnostic testing from biological samples, particularly in presence of interfering substances. Some embodiments relate to nucleic acid-based detection and identification of vulvovaginal candidiasis-associated *Candida* species, trichomoniasis-causing *Trichomonas vaginalis* and/or bacterial vaginosis-related bacteria from clinical vaginal swabs, sampled from women showing clinical symptoms of vaginitis and/or vaginosis using the compositions, kits and methods disclosed herein. In some embodiments, sexually transmitted diseases, including chlamydia, gonorrhea, trichomoniasis, are diagnosed by using nucleic acid-based compositions, kits and methods disclosed herein.

Description of the Related Art

*Candida* is a genus of yeast and is the most common cause of fungal infections worldwide. Many *Candida* species are found as a harmless commensal, part of a normal flora of a host and can be endosymbionts of hosts including humans. However, in the case of an imbalance or an immune compromisation of a host, *Candida* is known to invade and cause disease. Some *Candida* spp., such as *C. krusei*, and *C. glabrata*, are known to be associated with vulvovaginal candidiasis (VVC). *Trichomonas vaginalis* (*T. vaginalis*) is an anaerobic, flagellated protozoan parasite, which is the causative agent of trichomoniasis. Bacterial vaginosis (BV) is an infection of vagina caused by alteration in normal balance of bacteria in the vagina.

Sexually transmitted infections (STIs), such as chlamydia (CT), gonorrhea (GC), and trichomoniasis (TV), pose a large and increasing public health burden. Although most of these infections are asymptomatic, if left unaddressed they can have serious consequences including pelvic inflammatory disease (PID), ectopic pregnancies, infertility, preterm or low-birthweight infants, and increased risk of STI transmission or infection (including HIV) in males and females.

Targeted treatment based on accurate diagnosis of vaginal disorders and/or sexually transmitted diseases is necessary to improve patient quality of life and achieve better clinical outcomes. Assay platforms and methods, involving fluidic manipulations of functionalized particles for nucleic acid extraction, have been developed for diagnostic testing and therapeutic interventions of VVC, trichomoniasis, BV, CT, GC, and TV. Some such assays are sensitive to even traces of interfering substances present in the biological samples being tested. In particular, clinical vaginal swab samples can be contaminated with gels, such as over-the-counter personal care creams used by patients and clinical-use lubricants introduced in examination procedures prior to sampling. Many of the interfering gels contain polyelectrolytes, such as carbomers (polyacrylic acid), capable of interacting with the functionalized particles deployed in the assays for nucleic acid extraction. If transferred into an assay cartridge, the interfering gels can cause aggregation of functionalized particles in fluidic channels, clogging the fluidic channels, and/or inhibiting polymerase chain reaction (PCR) of target nucleic acids. Accordingly, in the presence of interfering substances, many nucleic acid-based assays produce not only more reporting errors (false-positives and false-negatives) but also increased non-reportable results (e.g., unresolved results due to internal control failures, indeterminate results due to excessive noise, etc.). For example, particle aggregation leads to loss of functionalization and can, thereby, reduce the assay sensitivity and increase the rates of unresolved results. Channel clogging can increase the rates of indeterminate results; and PCR inhibition can increase the false-negative rates.

SUMMARY

Standard buffers utilized in assays such as those discussed above are typically designed with the sole purpose of preserving biological samples after collection for subsequent diagnostic analysis. In view of the various adverse events associated with interfering substances commonly present in clinical samples, there is a compelling need for developing novel buffer compositions (and methods therewith) that will afford greater interference-robustness, while retaining clinical efficiency, to the on-chip sample processing and ensuing detection of vaginal disorders (e.g., vulvovaginal candidiasis, trichomoniasis, bacterial vaginosis, etc.). In the cases of the microfluidic assays as discussed in the preceding paragraph, there is a particular need with respect to preventing the occurrence and/or mitigating the consequences of particle aggregation, channel clogging and PCR inhibition. There is a further need for novel buffer compositions that are capable of compatibly working with various clinical workflows, leading to more prompt diagnoses, more effective treatments, and better patient outcomes.

Embodiments of the present disclosure relate to compositions, kits, and methods for nucleic acid-based detection and identification of vaginal disorders and/or sexually transmitted diseases, in particular, from vaginal samples containing interfering substances. Some disclosed embodiments relate to buffer compositions, kits, and methods for preventing or reducing aggregation of surface-functionalized particles, for example, those deployed in microfluidic PCR devices for nucleic-acid extraction and/or purification. Some embodiments can enhance efficiency of amplification of and/or detection for nucleic acids from vaginal pathogenic organisms. It will be understood by one of skill in the art that application of the compositions, kits, and methods described herein are not limited to a particular sample or a particular vaginal disorder.

A buffer composition is disclosed herein. In some embodiments, the buffer composition comprises: a conjugate pair of an acid and a base; a chelating agent or reducing agent; a non-ionic surfactant; a monovalent or divalent salt, selected from the group consisting of sodium salts, potassium salts, calcium salts, magnesium salts, and combinations thereof; and optionally a biocidal preservative, comprising one or more isothiazolones. In some embodiments, the conjugate pair comprises acetic acid and a salt thereof. In some embodiments, the conjugate pair comprises about 50 mM to about 150 mM acetic acid. In some embodiments, the conjugate pair comprises about 90 mM to about 110 mM acetic acid. In some embodiments, the conjugate pair comprises about 350 mM to 450 mM sodium acetate. In some embodiments, the conjugate pair can be present at a concentration in the range of about 400 mM to about 600 mM. In some embodiments, the conjugate pair comprises acetic acid and sodium acetate, or Tris-HCl. In some embodiments, the acetic acid is present at a concentration of no more than 200 mM and the sodium acetate can be present at a concentration of no less than 300 mM. In some embodiments, the buffer composition can be at a pH from about 4.0 to about 6.0 or about 1.0 to about 3.0. In some embodiments, the buffer composition can be at a pH of about 5.0. In some embodiments, the buffer composition can be at a pH of about or about 2.4. In some embodiments, the chelating agent can comprise EDTA. In some embodiments, the reducing agent comprises TCEP. In some embodiments, the chelating agent or reducing agent can be present at a concentration in the range of about 1 mM to about 20 mM. In some embodiments, the chelating agent is EDTA at a concentration of about 10 mM. In some embodiments, the reducing agent is TCEP at a concentration of about 15 mM. In some embodiments, the non-ionic surfactant can be selected from the group consisting of ethoxylated non-ionic surfactants, propoxylated non-ionic surfactants, co-ethoxylated-propoxylated non-ionic surfactants, and combinations thereof. In some embodiments, the non-ionic surfactant can be selected from the group consisting of ethoxylated sorbitan esters of mono-fatty acids, ethoxylated octylphenols, ethoxylated secondary C1 to C20 alcohols, co-ethoxylated-propoxylated seed oil alcohols, and combinations thereof. In some embodiments, the non-ionic surfactant can be selected from the group consisting of ethoxylated sorbitan esters of mono-fatty acids containing an average of 1 to 50 ethylene oxide units per surfactant, ethoxylated octylphenols containing an average of 1 to 20 ethylene oxide units per surfactant, ethoxylated secondary C1 to C20 alcohols containing an average of 1 to 20 ethylene oxide units per surfactant, co-ethoxylated-propoxylated seed oil alcohols containing an average of 1 to 20 propylene oxide units and 1 to 30 ethylene oxide units per surfactant, and combinations thereof. In some embodiments, the non-ionic surfactant can comprise one or more ethoxylated sorbitan esters of mono-fatty acids. In some embodiments, one or more ethoxylated sorbitan esters of mono-fatty acids can contain an average of 1 to 50 ethylene oxide units. In some embodiments, the non-ionic surfactant can comprise one or more ethoxylated secondary C1 to C20 alcohols. In some embodiments, one or more ethoxylated secondary C1 to C20 alcohols can contain an average of 1 to 20 ethylene oxide units. In some embodiments, the non-ionic surfactant can comprise one or more ethoxylated octylphenols. In some embodiments, one or more ethoxylated octylphenols can contain an average of 1 to 20 ethylene oxide units. In some embodiments, the non-ionic surfactant can comprise one or more co-ethoxylated-propoxylated seed oil alcohols. In some embodiments, one or more co-ethoxylated-propoxylated seed oil alcohols can comprise an average of 1 to 20 propylene oxide units and 1 to 30 ethylene oxide units. In some embodiments, the non-ionic surfactant is a Tergitol™ or Triton™ surfactant. In some embodiments, the non-ionic surfactant is Tergitol™ 15-S-9 or Triton™ X-100. In some embodiments, the non-ionic surfactant can be present at a concentration in the range of about 0.5% to 1.5% by weight of the buffer composition. In some embodiments, the non-ionic surfactant is present at a concentration in the range of about 1.0% by weight of the buffer composition. In some embodiments, the divalent salt can be a calcium salt. In some embodiments, the divalent salt can be $CaCl_2$). In some embodiments, the monovalent or divalent salt can be present at a concentration in the range of about 100 mM to about 300 mM. In some embodiments, the monovalent or divalent salt can be present at a concentration of about 200 mM. In some embodiments, the biocidal preservative can be present at a concentration in the range of about 0.03% by weight of the buffer composition. In some embodiments, the biocidal preservative can comprise about 1% to about 5% by weight one or more isothiazolones. In some embodiments, the biocidal preservative can comprise about 2% to about 4% by weight one or more isothiazolones. In some embodiments, the biocidal preservative can comprise about 1% to about 3% by weight one or more isothiazolones. In some embodiments, the one or more isothiazolones comprise chloromethylisothiazolinone and methylisothiazolinone. In some embodiments, the chloromethylisothiazolinone and methylisothiazolinone are at a weight ratio from about 1:1 to about 5:1. In some embodiments, the one or more isothiazolones comprise 5-chloro-2-methyl-4-isothiazolin-3-one and 2-methyl-4-isothiazolin-3-one at a weight ratio of about 3:1. In some embodiments, the biocidal preservative comprises one or more of a salt-free proprietary glycol and an alkyl carboxylate stabilizer. In some embodiments, the buffer composition does not contain a biocidal preservative. In some embodiments, the buffer composition is Example Buffer I, or Example Buffer II, or Example Buffer III.

The present disclosure also provides kits. In some embodiments, the kit comprises a buffer composition as described above and/or described elsewhere herein. In some embodiments, the kit comprises a sterile container housing the buffer composition. In some embodiments, the kit comprises a manual for diagnosing a condition associated with vaginal infections or inflammation. In some embodiments, the condition is vaginitis, or vaginosis, or a sexually transmitted disease, or a combination thereof. In some embodiments, the condition is vulvovaginal candidiasis (VVC), trichomoniasis, or bacterial vaginosis (BV), or a combination thereof. In some embodiments, the condition is a sexually transmitted disease, for example, chlamydia (CT), gonorrhea (GC), trichomoniasis (TV), or a combination thereof.

The present disclosure provides a method of preventing or reducing aggregation of surface-functionalized particles, comprising contacting a sample with a buffer composition as described above and/or described elsewhere herein. In some embodiments the sample comprises a plurality of surface-functionalized particles; and the level of aggregation of the plurality of surface-functionalized particles in the presence of the buffer composition is reduced as compared to the level of aggregation in the absence of the buffer composition. In some embodiments, the level of aggregation of the plurality of surface-functionalized particles in the presence of the buffer composition can be reduced by at least 1% as compared to the level of aggregation in the absence of the buffer composition. In some embodiments, the level of aggregation of the plurality of surface-functionalized particles in the presence of the buffer composition is reduced by at least 5% as compared to the level of aggregation in the absence of the buffer composition. In some embodiments, the level of aggregation of the plurality of surface-functionalized particles in the presence of the buffer composition is reduced by at least 10% as compared to the level of aggregation in the absence of the buffer composition. In some embodiments, the sample is a clinical sample. In some embodiments, the sample is a vaginal sample. In some embodiments, the sample is a clinical vaginal swab. In some embodiments, the sample is collected from vagina. In some embodiments, the sample is collected from a subject showing clinical symptoms of vaginitis, vaginosis, a sexually-transmitted disease (e.g., chlamydia (CT), gonorrhea (GC), trichomoniasis (TV)), or a combination thereof. In some embodiments, the sample is collected from a subject showing clinical symptoms of vaginitis, or vaginosis, or both. In some embodiment, the sample is collected from a subject showing clinical symptoms of chlamydia (CT), gonorrhea (GC), trichomoniasis (TV), or a combination thereof. In some embodiments, the sample can comprise a plurality of nucleic acids. In some embodiments, a plurality of nucleic acids is from one or more vulvovaginal candidiasis (VVC)-associated *Candida* species, trichomoniasis-causing *Trichomonas vaginalis*, one or more bacterial vaginosis (BV)-related bacteria, or a combination thereof. In some embodiments, one or more VVC-associated *Candida* species can comprise *Candida glabrata, Candida albicans, Candida tropicalis, C. dubliniensis, C. parapsilosis, Candida krusei*, or a combination thereof. In some embodiments, one or more BV-related bacteria can comprise *Lactobacillus* crispatus, *Lactobacillus jensenii, Gardnerella vaginalis*, Atopobium vaginae, Megasphaera Type 1, Megasphaera BVAB2, or a combination thereof. In some embodiments, the method can further comprise amplifying and/or detecting the plurality of nucleic acids, wherein the efficiency of amplification and/or detection of the plurality of nucleic acids is enhanced in the presence of the buffer composition as compared to the efficiency in the absence of the buffer composition. In some embodiments, the efficiency of amplification and/or detection of the plurality of nucleic acids is enhanced by at least 1% in the presence of the buffer composition as compared to the efficiency in the absence of the buffer composition. In some embodiments, the efficiency of amplification and/or detection of the plurality of nucleic acids is enhanced by at least 5% in the presence of the buffer composition as compared to the efficiency in the absence of the buffer composition. In some embodiments, the surface-functionalized particles can comprise an average diameter of less than 1 mm. In some embodiments, the surface-functionalized particles are configured for nucleic acid extraction, purification, amplification, detection, or combinations thereof. In some embodiments, the aggregation is induced by an interfering substance in the sample. In some embodiments, the aggregation can occur in a microfluidic channel. In some embodiments, the interfering substance is selected from the group consisting of lubricants, gels, creams, and combinations thereof. In some embodiments, the interfering substance can comprise a gel comprising one or more carbomers. In some embodiments, the interfering substance can comprise a gel that does not comprise any carbomers.

Alternative or additional embodiments described herein provide a buffer composition comprising one or more of the features of the foregoing description or of any description elsewhere herein.

Alternative or additional embodiments described herein provide a kit comprising one or more of the features of the foregoing description or of any description elsewhere herein.

Alternative or additional embodiments described herein provide a method of preventing or reducing aggregation of surface-functionalized particles comprising one or more of the features of the foregoing description or of any description elsewhere herein.

BRIEF DESCRIPTION OF THE DRAWINGS

FIGS. 2 to 4 illustrate an embodiment of the reduction of particle aggregation and the prevention of microfluidic clogging in the BD MAX™ PCR cartridges as achieved by use of an embodiment of the buffer composition disclosed herein (see Table 1 below).

FIGS. 2A-2B show photographs of embodiments of the BD MAX™ PCR cartridges, each of which has been utilized in a diagnostic testing of a clinical vaginal-swab sample that does not contain interfering gels.

FIGS. 3A-3B show embodiments of photographs of BD MAX™ PCR cartridges, each of which has been utilized in a diagnostic testing of a clinical vaginal-swab sample that contains a carbomer-based interfering gel, McKesson present at 10 μL. FIGS. 4A-4B show additional embodiments of photographs of BD MAX™ PCR cartridges utilized in testing an additional interfering gel E-Z brand (Medline Industries, Inc.) (FIGS. 4A-4B) present at 10 μL.

DETAILED DESCRIPTION

Figure 1:
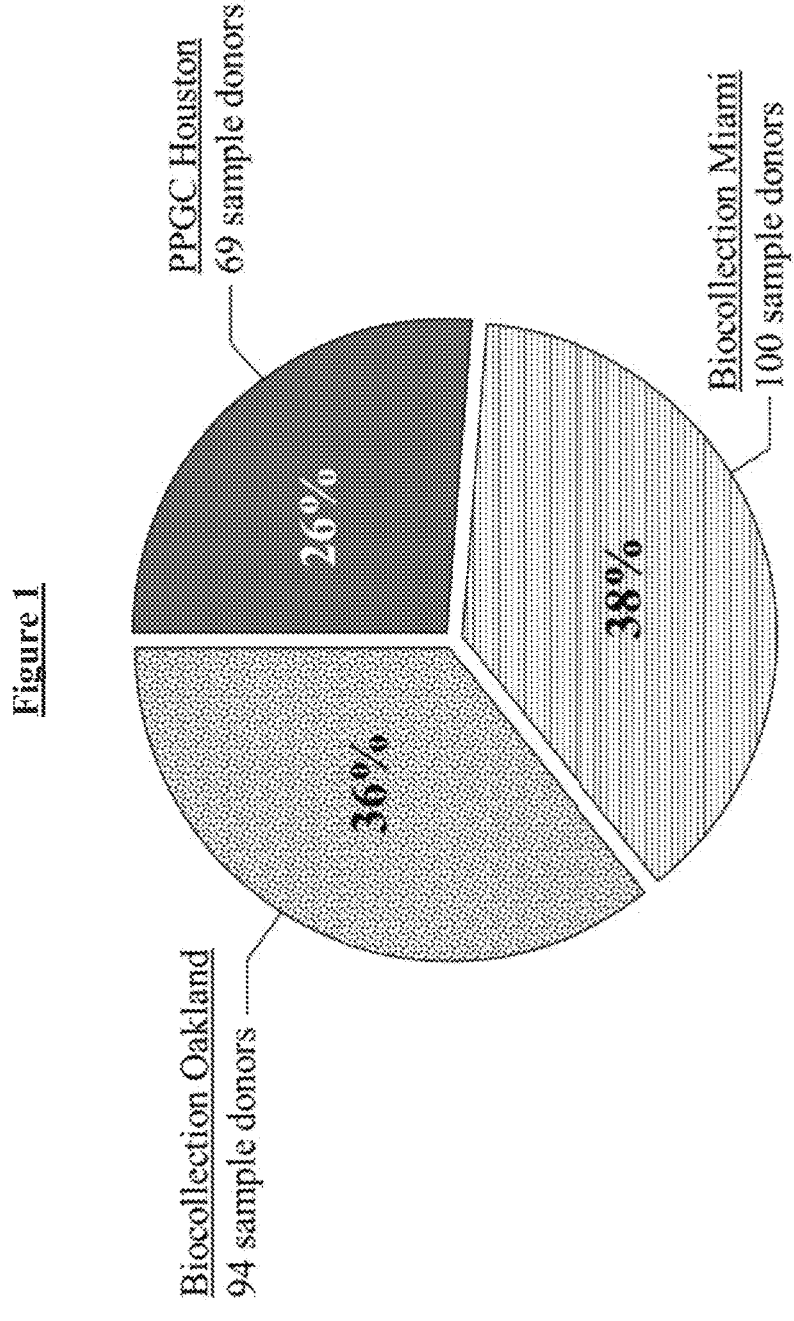
FIG. 1 shows a pie chart of the composition of 263 donors of clinical vaginal-swab samples, by geographical region, as studied in Examples 2 to 9.

The section headings used herein are for organizational purposes only and are not to be construed as limiting the subject matter described in any way. All literature and similar materials cited in this application including, but not limited to, patents, patent applications, articles, books, treatises, and internet web pages, regardless of the format of such literature and similar materials, are expressly incorporated by reference in their entirety for any purpose. In the event that one or more of the incorporated literature and similar materials defines or uses a term in such a way that it contradicts that term's use in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Provided herein are buffer compositions, kits, and methods for nucleic acid-based detection of vaginal disorders, for example, vulvovaginal candidiasis (VVC), trichomoniasis and/or bacterial vaginosis (BV). For example, buffer compositions that can prevent or reduce aggregation of surface-functionalized particles, for example, those deployed in microfluidic PCR cartridges for nucleic acid extraction, during assaying are provided to detect pathogenic organisms from clinical vaginal-swab samples in presence of interfering substances. In some embodiments, the buffer compositions can enhance or maintain efficiency of the nucleic acid-based detection, for example, for VVC-associated *Candida* species, trichomoniasis-causing *Trichomonas vaginalis* and/or BV-related bacteria.

As used herein, a "nucleic acid" has its plain an ordinary meaning in view of this disclosure, and refers to a polymeric compound comprising nucleosides or nucleoside analogs which have nitrogenous heterocyclic bases, or base analogs, linked together by nucleic acid backbone linkages (e.g., phosphodiester bonds) to form a polynucleotide. Non-limiting examples of nucleic acid include RNA, DNA, and analogs thereof. The nucleic acid backbone can include a variety of linkages, for example, one or more of sugar-phosphodiester linkages, peptide-nucleic acid bonds, phosphorothioate or methylphosphonate linkages or mixtures of such linkages in a single oligonucleotide. Sugar moieties in the nucleic acid are either ribose or deoxyribose, or similar compounds with known substitutions. Conventional nitrogenous bases (e.g., A, G, C, T, U), known base analogs (e.g., inosine), derivatives of purine or pyrimidine bases and "abasic" residues (i.e., no nitrogenous base for one or more backbone positions) are included in the term nucleic acid. That is, a nucleic acid can include only conventional sugars, bases and linkages found in RNA and DNA, or include both conventional components and substitutions (e.g., conventional bases and analogs linked via a methoxy backbone, or conventional bases and one or more base analogs linked via an RNA or DNA backbone).

As used herein, a "conjugate pair" has its plain an ordinary meaning in view of this disclosure, and refers to an acid (HA) and a base ($A^-$) that differ by one proton ($H^+$). For example, potassium phosphate monobasic ($KH_2PO_4$) and potassium phosphate dibasic ($K_2HPO_4$) are a conjugate pair. As another example, acetic acid and sodium acetate ($CH_3COONa$) are also a conjugate pair.

As used herein, the term "sensitivity," has its plain and ordinary meaning in view of this disclosure, and when referring to performance of a testing method, is true positives divided by the sum of true positives and false negatives. One of skill in the art will understand that the terms "recall," "hit rate," and "true positive rate (TPR)," when referring to performance of a testing method, are the same as "sensitivity."

As used herein, the term "specificity," has its plain an ordinary meaning in view of this disclosure, and when referring to performance of a testing method, is true negatives divided by the sum of true negatives and false positives. One of skill in the art will understand that the terms "selectivity," and "true negative rate (TPR)," when referring to performance of a testing method, are the same as "specificity."

As used herein, the term "accuracy," has its plain an ordinary meaning in view of this disclosure, and when referring to performance of a testing method, is the sum of true positives and true negatives divided by the sum of true positives, false positives, true negatives, and false negatives.

As used herein, "$C_a$ to $C_b$" in which "a" and "b" are integers refers to the number of carbon atoms in compound.

Buffer Compositions

Some embodiments disclosed herein provide a buffer composition. In some embodiments, the buffer composition comprises a conjugate pair of an acid and a base, a chelating agent, a non-ionic surfactant, a monovalent or divalent salt, and optionally a biocidal preservative. In some embodiments, the buffer composition comprises a conjugate pair of an acid and a base, a chelating agent, a non-ionic surfactant, a monovalent or divalent salt, and optionally a biocidal preservative in any of the amounts or ranges of amounts disclosed herein, including the following.

In some embodiments, the base of the conjugate pair is a salt of the acid. In some embodiments, the acid comprises acetic acid. In some embodiments, the base comprises a salt of the acetic acid. In some embodiments, the conjugate pair comprises acetic acid and a salt thereof. In some embodiments, the base comprises sodium acetate. In some embodiments, the conjugate pair comprises acetic acid and sodium acetate. In some embodiments the buffer comprises Tris-HCl. In some embodiments, the concentration of the acid (e.g., acetic acid) is a concentration of, or a concentration of about, or a concentration of no more than, or a concentration of no more than about, or a concentration of no less than, or a concentration of no less than about, 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 105 mM, 110 mM, 115 mM, 120 mM, 125 mM, 130 mM, 135 mM, 140 mM, 145 mM, 150 mM, 155 mM, 160 mM, 165 mM, 170 mM, 175 mM, 180 mM, 185 mM, 190 mM, 195 mM, 200 mM, 205 mM, 210 mM, 215 mM, 220 mM, 225 mM, 230 mM, 235 mM, 240 mM, 245 mM, 250 mM, 255 mM, 260 mM, 265 mM, 270 mM, 275 mM, 280 mM, 285 mM, 290 mM, 295 mM, 300 mM, 305 mM, 310 mM, 315 mM, 320 mM, 325 mM, 330 mM, 335 mM, 340 mM, 345 mM, 350 mM, 355 mM, 360 mM, 365 mM, 370 mM, 375 mM, 380 mM, 385 mM, 390 mM, 395 mM, 400 mM, 405 mM, 410 mM, 415 mM, 420 mM, 425 mM, 430 mM, 435 mM, 440 mM, 445 mM, 450 mM, 455 mM, 460 mM, 465 mM, 470 mM, 475 mM, 480 mM, 485 mM, 490 mM, 495 mM, or 500 mM, or a range between any two of these values. In some embodiments, the concentration of the acid (e.g., acetic acid), is 5 mM to 100 mM, 5 mM to 250 mM, 200 to 400 mM, 250 mM to 500 mM, 300 mM to 500 mM or 400 mM to 500 mM. In some embodiments, the concentration of the base (e.g., sodium acetate) is a concentration of, or a concentration of about, or a concentration of no more than, or a concentration of no more than about, or a concentration of no less than, or a concentration of no less than about, 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 105 mM, 110 mM, 115 mM, 120 mM, 125 mM, 130 mM, 135 mM, 140 mM, 145 mM, 150 mM, 155 mM, 160 mM, 165 mM, 170 mM, 175 mM, 180 mM, 185 mM, 190 mM, 195 mM, 200 mM, 205 mM, 210 mM, 215 mM, 220 mM, 225 mM, 230 mM, 235 mM, 240 mM, 245 mM, 250 mM, 255 mM, 260 mM, 265 mM, 270 mM, 275 mM, 280 mM, 285 mM, 290 mM, 295 mM, 300 mM, 305 mM, 310 mM, 315 mM, 320 mM, 325 mM, 330 mM, 335 mM, 340 mM, 345 mM, 350 mM, 355 mM, 360 mM, 365 mM, 370 mM, 375 mM, 380 mM, 385 mM, 390 mM, 395 mM, 400 mM, 405 mM, 410 mM, 415 mM, 420 mM, 425 mM, 430 mM, 435 mM, 440 mM, 445 mM, 450 mM, 455 mM, 460 mM, 465 mM, 470 mM, 475 mM, 480 mM, 485 mM, 490 mM, 495 mM, or 500 mM, or a range between any two of these values. In some embodiments, the concentration of the base (e.g., sodium acetate), is 5 mM to 100 mM, 5 mM to 250 mM, 200 to 400 mM, 250 mM to 500 mM, 300 mM to 500 mM or 400 mM to 500 mM. In some embodiments, the conjugate pair comprises about 350 mM to 450 mM sodium acetate. In some embodiments, the conjugate pair comprises about 50 mM to about 150 mM acetic acid. In some embodiments, the conjugate pair comprises about 90 mM to about 110 mM acetic acid. In some embodiments, the conjugate pair is present at a concentration of, or a concentration of about, or a concentration of no more than, or a concentration of no more than about, or a concentration of no less than, or a concentration of no less than about, 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 105 mM, 110 mM, 115 mM, 120 mM, 125 mM, 130 mM, 135 mM, 140 mM, 145 mM, 150 mM, 155 mM, 160 mM, 165 mM, 170 mM, 175 mM, 180 mM, 185 mM, 190 mM, 195 mM, 200 mM, 205 mM, 210 mM, 215 mM, 220 mM, 225 mM, 230 mM, 235 mM, 240 mM, 245 mM, 250 mM, 255 mM, 260 mM, 265 mM, 270 mM, 275 mM, 280 mM, 285 mM, 290 mM, 295 mM, 300 mM, 305 mM, 310 mM, 315 mM, 320 mM, 325 mM, 330 mM, 335 mM, 340 mM, 345 mM, 350 mM, 355 mM, 360 mM, 365 mM, 370 mM, 375 mM, 380 mM, 385 mM, 390 mM, 395 mM, 400 mM, 405 mM, 410 mM, 415 mM, 420 mM, 425 mM, 430 mM, 435 mM, 440 mM, 445 mM, 450 mM, 455 mM, 460 mM, 465 mM, 470 mM, 475 mM, 480 mM, 485 mM, 490 mM, 495 mM, 500 mM, 505 mM, 510 mM, 515 mM, 520 mM, 525 mM, 530 mM, 535 mM, 540 mM, 545 mM, 550 mM, 555 mM, 560 mM, 565 mM, 570 mM, 575 mM, 580 mM, 585 mM, 590 mM, 595 mM, 600 mM, 605 mM, 610 mM, 615 mM, 620 mM, 625 mM, 630 mM, 635 mM, 640 mM, 645 mM, 650 mM, 655 mM, 660 mM, 665 mM, 670 mM, 675 mM, 680 mM, 685 mM, 690 mM, 695 mM, 700 mM, 705 mM, 710 mM, 715 mM, 720 mM, 725 mM, 730 mM, 735 mM, 740 mM, 745 mM, 750 mM, 755 mM, 760 mM, 765 mM, 770 mM, 775 mM, 780 mM, 785 mM, 790 mM, 795 mM, 800 mM, 805 mM, 810 mM, 815 mM, 820 mM, 825 mM, 830 mM, 835 mM, 840 mM, 845 mM, 850 mM, 855 mM, 860 mM, 865 mM, 870 mM, 875 mM, 880 mM, 885 mM, 890 mM, 895 mM, or 900 mM, or a range between any two of these values. In some embodiments, the concentration of the conjugate pair (e.g., aceitic acid and sodium acetate or Tris-HCL), is 5 mM to 100 mM, 5 mM to 250 mM, 200 to 400 mM, 250 mM to 500 mM, 300 mM to 500 mM, 400 mM to 500 mM, 5 mM to 1 M, 300 mM to 700 mM, 500 mM to 900 mM, 750 mM to 1 M or 800 mM to 1 M. In some embodiments, the conjugate pair is present at a concentration in the range of about 400 mM to about 600 mM. In some embodiments, the conjugate pair comprises acetic acid and sodium acetate. In some embodiments, the acetic acid is present at a concentration of no more than 200 mM and the sodium acetate is present at a concentration of no less than 300 mM. In some embodiments the conjugate is Tris-HCl at a concentration of 10 mM.

In some embodiments, the pH of the buffer composition is, or is about, or is no more than, or is no more than about, or is no less than, or is no less than about, 1.0, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0, or a range between any of these values. In some embodiments, the buffer composition is at a pH from about 4.0 to about 6.0. In some embodiments, the buffer composition is at a pH of about 5.0.

In some embodiments the chelating agent includes, but is not limited to, ethylenediaminetetraacetic acid (EDTA), ethylenediamine, amino acids such as glutamic acid and histidine, organic diacids such as oxalic acid, malonic acid, succinic acid, and the like, and pharmaceutically acceptable salts of the foregoing. In some embodiments, the chelating agent comprises EDTA. In some embodiments, the concentration of the chelating agent (e.g. EDTA) is, or is about, or is no more than, or is no more than about, or is no less than, or is no less than about, 0.2 mM, 0.5 mM, 0.8 mM, 0.9 mM, 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, or 20 mM, or a range between any two of these values. In some embodiments, the chelating agent is present at a concentration in the range of about 1 mM to about 20 mM, 0.2 mM to 2 mM, 1 mM to 7 mM, 16 mM to 20 mM, 10 mM to 20 mM, or 4 mM to 8 mM. In some embodiments the concentration of chelating agent, (e.g., EDTA) is about 10 mM.

In some embodiments, the non-ionic surfactant is selected from the group consisting of ethoxylated non-ionic surfactants, propoxylated non-ionic surfactants, co-ethoxylated-propoxylated non-ionic surfactants, and combinations thereof. In some embodiments, the non-ionic surfactant is selected from the group consisting of ethoxylated sorbitan esters of mono-fatty acids, ethoxylated octylphenols, ethoxylated secondary C1 to C20 alcohols, co-ethoxylated-propoxylated seed oil alcohols, and combinations thereof. In some embodiments, the non-ionic surfactant is selected from the group consisting of ethoxylated sorbitan esters of mono-fatty acids containing an average of 1 to 50 ethylene oxide units per surfactant, ethoxylated octylphenols containing an average of 1 to 20 ethylene oxide units per surfactant, ethoxylated secondary C1 to C20 alcohols containing an average of 1 to 20 ethylene oxide units per surfactant, co-ethoxylated-propoxylated seed oil alcohols containing an average of 1 to 20 propylene oxide units and 1 to 30 ethylene oxide units per surfactant, and combinations thereof. In some embodiments, the non-ionic surfactant comprises one or more ethoxylated sorbitan esters of mono-fatty acids. In some embodiments, one or more ethoxylated sorbitan esters of mono-fatty acids contain an average of 1 to 50 ethylene oxide units. In some embodiments, the non-ionic surfactant comprises a Tween surfactant. In some embodiments, the non-ionic surfactant comprises Tween 20 surfactant, Tween 40 surfactant, Tween 60 surfactant, Tween 80 surfactant, or a combination thereof. In some embodiments the surfactant is an ECOSURF™ surfactant (Dow Chemical Co.), e.g., ECOSURF™ SA-4, SA-7, SA-9 or SA-15 surfactant. In some embodiments, the non-ionic surfactant comprises one or more ethoxylated secondary C1 to C20 alcohols. In some embodiments, one or more ethoxylated secondary C1 to C20 alcohols contains an average of 1 to 20 ethylene oxide units. In some embodiments, the non-ionic surfactant comprises a Tergitol™ surfactant (Signma-Aldrich), for example, Tergitol™ 15-S-9 surfactant. In some embodiments, the non-ionic surfactant comprises one or more ethoxylated octylphenols. Some of the one or more ethoxylated octylphenols contain an average of 1 to 20 ethylene oxide units. In some embodiments, the non-ionic surfactant comprises a Triton surfactant, for example, Triton X-100 surfactant. In some embodiments, the non-ionic surfactant comprises one or more co-ethoxylated-propoxylated seed oil alcohols. Some of the one or more co-ethoxylated-propoxylated seed oil alcohols comprise an average of 1 to 20 propylene oxide units and 1 to 30 ethylene oxide units. In some embodiments, the non-ionic surfactant comprises an EcoSurf™ surfactant. The non-ionic surfactant is present in the buffer composition at a concentration of, or at a concentration of about, or at a concentration of no more than, or at a concentration of no more than about, or at a concentration of no less than, or at a concentration of no less than about, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, or 3.0%, or a range between any two of these values. In some embodiments, the non-ionic surfactant is present at a concentration in the range of about 0.5% to 1.5%, 0.1% to 3.0%, 0.8% to 1.9%, 1.0% to 2.0%, 2.5% to 3% or 0.7% to 2.6%, by weight of the buffer composition. In some embodiments, the non-ionic surfactant is present at a concentration in the range of about 1.0% by weight of the buffer composition.

In some embodiments, the monovalent or divalent salt is selected from the group consisting of a sodium salt, a potassium salt, a calcium salt, a magnesium salt, or a combinations thereof. In some embodiments, the divalent salt is a calcium salt. In some embodiments, the divalent salt is $CaCl_2$. In some embodiments, the monovalent or divalent salt is present at a concentration of, or at a concentration of about, or at a concentration of no more than, or at a concentration of no more than about, or at a concentration of no less than, or at a concentration of no less than about, 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 105 mM, 110 mM, 115 mM, 120 mM, 125 mM, 130 mM, 135 mM, 140 mM, 145 mM, 150 mM, 155 mM, 160 mM, 165 mM, 170 mM, 175 mM, 180 mM, 185 mM, 190 mM, 195 mM, 200 mM, 205 mM, 210 mM, 215 mM, 220 mM, 225 mM, 230 mM, 235 mM, 240 mM, 245 mM, 250 mM, 255 mM, 260 mM, 265 mM, 270 mM, 275 mM, 280 mM, 285 mM, 290 mM, 295 mM, 300 mM, 305 mM, 310 mM, 315 mM, 320 mM, 325 mM, 330 mM, 335 mM, 340 mM, 345 mM, 350 mM, 355 mM, 360 mM, 365 mM, 370 mM, 375 mM, 380 mM, 385 mM, 390 mM, 395 mM, 400 mM, 405 mM, 410 mM, 415 mM, 420 mM, 425 mM, 430 mM, 435 mM, 440 mM, 445 mM, 450 mM, 455 mM, 460 mM, 465 mM, 470 mM, 475 mM, 480 mM, 485 mM, 490 mM, 495 mM, or 500 mM, or a range between any two of these values. In some embodiments, the concentration of the monovalent or divalent salt (e.g., $CaCl_2$)), is 5 mM to 100 mM, 5 mM to 250 mM, 200 to 400 mM, 250 mM to 500 mM, 300 mM to 500 mM or 400 mM to 500 mM. In some embodiments, the monovalent or divalent salt is present at a concentration in the range of about 100 mM to about 300 mM. In some embodiments, the monovalent or divalent salt is present at a concentration of about 200 mM.

In some embodiments, the buffer composition optionally includes a biocidal preservative. In some embodiments, the biocidal preservative comprises one or more isothiazolones. In some embodiments, the biocidal preservative is present at a concentration of, or at a concentration of about, or at a concentration of no more than, or at a concentration of no more than about, or at a concentration of no less than, or at a concentration of no less than about, 0.01%, 0.015%, 0.02%, 0.025%, 0.03%, 0.035%, 0.04%, 0.045%, 0.05%, 0.06%, 0.07%, 0.08%, 0.09%, or 0.1% by weight of the buffer composition, or a range between any two of these values. In some embodiments, the biocidal preservative is present at a concentration of about 0.01% to 0.1%, 0.01% to 0.03%, 0.025% to 0.045%, 0.05% to 0.1%, 0.07% to 0.01% or 0.04% to 0.08% by weight of the buffer composition. In some embodiments, the biocidal preservative is present at a concentration of about 0.03% by weight of the buffer composition. In some embodiments, the biocidal preservative is ProClin™ 300. In some embodiments, the biocidal preservative ProClin™ 300 is present at a concentration of about 0.03% by weight of the buffer composition. In some embodiments, the biocidal preservative comprises, or comprises about, or comprises no more than, or comprises no more than about, or comprises no less than, or comprises no less than about, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, or 6.0% by weight of one or more isothiazolones, or a range between any two of these values. In some embodiments, the biocidal preservative is present at a concentration of about 0.1% to 6.0%, 0.1% to 3.0%, 1.0% to 4.0%, 3% to 6%, 5% to 6% or 2% to 5% by weight of the buffer composition. In some embodiments, the biocidal preservative comprises about 1% to about 5% by weight one or more isothiazolones. In some embodiments, the biocidal preservative comprises about 2% to about 4% by weight one or more isothiazolones. In some embodiments, the biocidal preservative comprises about 1% to about 3% by weight one or more isothiazolones. In some embodiments, the one or more isothiazolones comprise chloromethylisothiazolinone and methylisothiazolinone. In some embodiments, the chloromethylisothiazolinone and methylisothiazolinone are at a weight ratio of, or a weight ratio of about, or a weight ratio of no more than, or a weight ratio of no more than about, or a weight ratio of no less than, or a weight ratio of no less than about, 1:1, 1.5:1, 2:1, 2.5:1 3:1, 3:5:1, 4:1, 4.5:1, 5:1, 5.5:1, 6:1, 6.5:1, 7:1, 7.5:1, 8:1, 8.5:1, 9:1, 9.5:1, or 10:1, or a range between any two of these values. In some embodiments, the chloromethylisothiazolinone and methylisothiazolinone are at a weight ratio from about 1:1 to about 5:1. In some embodiments, the one or more isothiazolones comprise 5-chloro-2-methyl-4-isothiazolin-3-one and 2-methyl-4-isothiazolin-3-one at a weight ratio of about 3:1. In some embodiments, the biocidal preservative comprises one or more of a salt-free proprietary glycol and an alkyl carboxylate stabilizer. In some embodiments, the buffer composition is used to preserve the sample before testing. In some embodiments, the buffer composition does not contain a biocidal preservative.

In some embodiments, buffer composition includes a reducing agent. In some embodiments the reducing agent is selected from the group consisting of dithiothreitol (DTT), β-mercaptoethanol, and TCEP (tris(2-carboxyethyl)phosphine). In some embodiments the reducing agent is TCEP (tris(2-carboxyethyl)phosphine). In some embodiments, the concentration of the reducing agent (e.g. TCEP) is, or is about, or is no more than, or is no more than about, or is no less than, or is no less than about, 0.2 mM, 0.5 mM, 0.8 mM, 0.9 mM, 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 25 mM, 30 mM, 40 mM, or 50 mM, or a range between any two of these values. In some embodiments, the reducing agent is present at a concentration in the range of 1 mM to 50 mM, 1 mM to 30 mM, 10 mM to 20 mM. In some embodiments the concentration of chelating agent, (e.g., TCEP) is about 15 mM.

Exemplary Buffer Compositions

The following are non-limiting exemplary buffer compositions. In some embodiments, the buffer comprises the components of Buffers #1, #2, or #3:

| Component | Buffer #1 | Buffer #2 | Buffer #3 |
|---|---|---|---|
| Acid-base pair | 5-500 mM acid<br>5-500 mM base | 10-200 mM acid<br>200-400 mM base | 50-150 mM acid<br>350-450 mM base |
| Chelating agent | 0.2-20 mM | 5-15 mM | 8-12 mM |

-continued

| Component | Buffer #1 | Buffer #2 | Buffer #3 |
|---|---|---|---|
| Surfactant | 0.1-3.0% | 0.25-1.5% | 0.5-1% |
| Monovalent or divalent salt | 5-500 mM | 100-300 mM | 150-250 mM |
| pH range | 4.0-6.0 | 4.0-6.0 | 4.8-5.2 |
| Biocidal preservative (optional) | 0.01-6.0% | 0.01-0.1% | 0.025-0.035% |

In some embodiments of Buffers #1-3 above, the acid-base pair is selected from the group consisting of acetic acid/sodium acetate and Tris-HCl, the chelating agent is selected from the group consisting of ethylenediaminetetraacetic acid (EDTA), ethylenediamine, amino acids such as glutamic acid and histidine, organic diacids such as oxalic acid, malonic acid, succinic acid, and the like, the surfactant is selected from the group consisting of ethoxylated non-ionic surfactants, propoxylated non-ionic surfactants, co-ethoxylated-propoxylated non-ionic surfactants, and combinations thereof, the monovalent or divalent salt is selected from the group consisting of a sodium salt, a potassium salt, a calcium salt, a magnesium salt, or a combinations thereof, and the biocidal preservative comprises one or more isothiazolones. In some embodiments of Buffers #1-3 above, the acid-base pair is acetic acid/sodium acetate, the chelating agent is EDTA, the surfactant is Tergitol™ 15-S-9, Triton X-100™, a Tween™ surfactant or an Ecosurf™ surfactant, the divalent salt is $CaCl_2$), and the biocidal preservative is a combination of chloromethylisothiazolinone and methylisothiazolinone. In some embodiments of Buffers #1-3 above, the acid-base pair is acetic acid/sodium acetate, the chelating agent is EDTA, the surfactant is Tergitol™ 15-S-9 or Triton X-100™, the divalent salt is $CaCl_2$), and the biocidal preservative is a combination of chloromethylisothiazolinone and methylisothiazolinone. In some embodiments of Buffers #1-3 above, the acid-base pair is acetic acid/sodium acetate, the chelating agent is EDTA, the surfactant is Tergitol™ 15-S-9 or Triton X-100™, the divalent salt is $CaCl_2$), and the biocidal preservative is ProClin™ 300. In some embodiments of Buffers #1-3 above, the acid-base pair is acetic acid/sodium acetate, the chelating agent is EDTA, the surfactant is Tergitol™ 15-S-9 or Triton X-100™, the divalent salt is $CaCl_2$), and the biocidal preservative is ProClin™ 300. In some embodiments of Buffers #1-3 above, the acid-base pair is acetic acid/sodium acetate, the chelating agent is EDTA, the surfactant is Tergitol™ 15-S-9, the divalent salt is $CaCl_2$), and the biocidal preservative is ProClin™ 300. In some embodiments of Buffers #1-3 above, the acid-base pair is acetic acid/sodium acetate, the chelating agent is EDTA, the surfactant is Triton X-100™, the divalent salt is $CaCl_2$), and the biocidal preservative is ProClin™ 300. In some embodiments of Buffers #1-3, including those above and herein, the buffer composition does not contain a biocidal preservative.

In some embodiments, the buffer comprises the components of Buffers #4, #5, or #6:

| Component | Buffer #4 | Buffer #5 | Buffer #6 |
|---|---|---|---|
| Acid-base pair | 0.1-50 mM base | 1-25 mM base | 5-15 mM base |

-continued

| Component | Buffer #4 | Buffer #5 | Buffer #6 |
|---|---|---|---|
| Surfactant | 0.1-3.0% | 0.25-2% | 0.5-1.5% |
| Reducing Agent | 1-50 mM | 1-30 mM | 10-20 mM |
| Monovalent or divalent salt | 5-500 mM | 50-200 mM | 100-150 mM |
| pH range | 1.0-4.0 | 1.5-3.5 | 2.2-2.6 |
| Biocidal preservative (optional) | 0.01-6.0% | 0.01-0.1% | 0.025-0.035% |

In some embodiments of Buffers #4-6 above, the acid-base pair is selected from the group consisting of acetic acid/sodium acetate and Tris-HCl, the surfactant is selected from the group consisting of ethoxylated non-ionic surfactants, propoxylated non-ionic surfactants, co-ethoxylated-propoxylated non-ionic surfactants, and combinations thereof, the reducing agent is selected from β-mercaptoethanol and TCEP (tris(2-carboxyethyl)phosphine), and the monovalent or divalent salt is selected from the group consisting of a sodium salt, a potassium salt, a calcium salt, a magnesium salt, or combinations thereof. In some embodiments of Buffers #4-6 above, the acid-base pair is acetic Tris-HCl, the surfactant is Tergitol™ 15-S-9, Triton X-100™, a Tween™ surfactant or an Ecosurf™ surfactant, the reducing agent is selected from the group consisting of β-mercaptoethanol and TCEP, and the monovalent or divalent salt is a calcium salt. In some embodiments of Buffers #4-6 above, the acid-base pair is Tris-HCl, the surfactant is Tergitol™ 15-S-9 or Triton X-100™, the reducing agent is TCEP (tris(2-carboxyethyl)phosphine), and the monovalent or divalent salt is $CaCl_2$. In some embodiments of Buffers #4-6 above, the acid-base pair is Tris-HCl, the surfactant is Triton X-100™, the reducing agent is TCEP, and the monovalent or divalent salt is $CaCl_2$. In some embodiments, the buffer composition comprises Tris-HCl buffer at 10 mM, TCEP 15 mM, 1% Triton-X100, $CaCl_2$ 50-150 mM, pH 2.4±0.2 In some embodiments of Buffers #4-6, including those above and herein, the buffer contains a biocidal preservative as disclosed herein. In some embodiments the biocidal preservative is ProClin™ 300. In some embodiments the biocidal preservative is ProClin™ 300 in an amount of 0.03%. In some embodiments of Buffers #4-6, including those above and herein, the buffer composition does not contain a biocidal preservative.

In some embodiments the buffer is Example Buffer I or Example Buffer II:

| Component | Example Buffer I | Example Buffer II |
|---|---|---|
| Acid-base pair | 105 mM acetic acid 395 mM $CH_3COONa$ | 105 mM acetic acid 395 mM $CH_3COONa$ |
| Chelating agent | 10 mM EDTA | 10 mM EDTA |
| Surfactant | 1% Tergitol ™ 15-S-9 | 0.5% Triton X-100 |
| Monovalent or divalent salt | 200 mM $CaCl_2$ | 200 mM $CaCl_2$ |
| pH range | (approximately 5.0) | (approximately 5.0) |
| Biocidal preservative | 0.03% ProClin ™ 300 | 0.03% ProClin ™ 300 |

In some embodiments the buffer is Example Buffer III:

| Component | Example Buffer III |
|---|---|
| Acid-base Pair | 10 mM Tris-HCl |
| Surfactant | 1% Triton X-100 |
| Reducing Agent | 15 mM TCEP |
| Monovalent or divalent salt | 50-150 mM $CaCl_2$ |
| pH range | 2.4 ± 0.2 |

Kits

Some of the embodiments disclosed herein provide a kit. In some embodiments, the kit comprises a buffer composition as described above or described elsewhere herein. In some embodiments, the kit comprises a sterile container housing the buffer composition. In some embodiments, the kit further comprises a microfluidic cartridge. In some embodiments, the microfluidic cartridge is configured to facilitate processing and detection of nucleic acids. In some embodiments, the microfluidic cartridge is disposable. In some embodiments, the kit comprises a manual for diagnosing a condition associated with vaginal infections or inflammation. In some embodiments, the condition is vaginitis, or vaginosis, or a combination thereof. In some embodiments, the condition is vulvovaginal candidiasis (VVC), trichomoniasis, or bacterial vaginosis (BV), or a combination thereof. In some embodiments, the condition is a sexually transmitted disease, for example, chlamydia (CT), gonorrhea (GC), trichomoniasis (TV), or a combination thereof.

Methods

Some of the embodiments disclosed herein provide a method of preventing or reducing aggregation of surface-functionalized particles, comprising contacting a sample with a buffer composition as described above in the "Buffer Compositions" section or described elsewhere herein. In some embodiments, the sample comprises a plurality of surface-functionalized particles; and the level of aggregation of the plurality of surface-functionalized particles in the presence of the buffer composition is reduced as compared to the level of aggregation in the absence of the buffer composition.

In some embodiments, the level of aggregation of the plurality of surface-functionalized particles in the presence of the buffer composition is reduced by, or is reduced by about, or is reduced by at least, or is reduced by at least about, or is reduced by at most, or is reduced by at most about, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100%, or a range between any two of these values, as compared to the level of aggregation in the absence of the buffer composition. In some embodiments, the level of aggregation of the plurality of surface-functionalized particles in the presence of the buffer composition is reduced by at least 1% as compared to the level of aggregation in the absence of the buffer composition. In some embodiments, the level of aggregation of the plurality of surface-functionalized particles in the presence of the buffer composition is reduced by at least 5% as compared to the level of aggregation in the absence of the buffer composition. In some embodiments, the level of aggregation of the plurality of surface-functionalized particles in the presence of the buffer composition is reduced by at least 10% as compared to the level of aggregation in the absence of the buffer composition. In some embodiments, the level of aggregation of the plurality of surface-functionalized particles in the presence of the buffer composition is reduced by 1-5%, 1-10%, 1-20%, 1-30%, 1-40%, 1-50%, 1-60%, 1-70%, 1-80%, 1-90%, 5-10%, 5-20%, 5-30%, 5-40%, 5-50%, 5-60%, 5-70%, 5-80%, 5-90%, 10-20%, 10-30%, 10-40%, 10-50%, 10-60%, 10-70%, 10-80%, or 10-90%, as compared to the level of aggregation in the absence of the buffer composition. In some embodiments, the level of particle aggregation is measured by using digital image processing, wherein the size of particle aggregates are determined by measuring their diameters or 2-dimensional areas on the image(s).

In some embodiments, the sample is a clinical sample. In some embodiments, the sample is a vaginal sample. In some embodiments, the sample is a clinical vaginal swab. In some embodiments, the sample is collected from vagina. In some embodiments, the sample is collected from a subject showing clinical symptoms of vaginitis, or vaginosis, or both. In some embodiments, the sample comprises a plurality of nucleic acids. In some embodiments, the sample comprises a plurality of nucleic acids from one or more vulvovaginal candidiasis (VVC)-associated *Candida* species, trichomoniasis-causing *Trichomonas vaginalis*, one or more bacterial vaginosis (BV)-related bacteria, or a combination thereof. In some embodiments, one or more VVC-associated *Candida* species comprise *Candida glabrata, Candida albicans, Candida tropicalis, C. dubliniensis, C. parapsilosis, Candida krusei*, or a combination thereof. In some embodiments, one or more BV-related bacteria comprise *Lactobacillus* crispatus, *Lactobacillus jensenii, Gardnerella vaginalis*, Atopobium vaginae, Megasphaera Type 1, Megasphaera BVAB2, or a combination thereof.

In some embodiments, the method further comprises amplifying and/or detecting the plurality of nucleic acids, wherein the efficiency of amplification and/or detection of the plurality of nucleic acids is enhanced in the presence of the buffer composition as compared to the efficiency in the absence of the buffer composition. In some embodiments, the efficiency of amplification and/or detection of the plurality of nucleic acids is enhanced by, or is enhanced by about, or is enhanced by at least, or is enhanced by at least about, or is enhanced by at most, or is enhanced by at most about, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%, or a range between any two of these values, as compared to the efficiency in the absence of the buffer composition. In some embodiments, the efficiency of amplification and/or detection of the plurality of nucleic acids is enhanced by at least 1% in the presence of the buffer composition as compared to the efficiency in the absence of the buffer composition. In some embodiments, the efficiency of amplification and/or detection of the plurality of nucleic acids is enhanced by at least 5% in the presence of the buffer composition as compared to the efficiency in the absence of the buffer composition. In some embodiments, the efficiency of amplification and/or detection of the plurality of nucleic acids is enhanced by 1-10%, 1-20%, 1-30%, 1-40%, 1-50%, 1-60%, 1-70%, 1-80%, or 1-90%, 5-10%, 5-20%, 5-30%, 5-40%, 5-50%, 5-60%, 5-70%, 5-80%, 5-90%, 10-20%, 10-30%, 10-40%, 10-50%, 10-60%, 10-70%, 10-80%, or 10-90%, in the presence of the buffer composition as compared to the efficiency in the absence of the buffer composition.

In some embodiments, the surface-functionalized particles comprise an average diameter of less than 1 mm. In some embodiments, the surface-functionalized particles are configured for nucleic acid extraction, purification, amplification, detection, or combinations thereof. In some embodiments, the aggregation is induced by an interfering substance in the sample. In some embodiments, the aggregation occurs in a microfluidic channel.

In some embodiments, the interfering substance is selected from the group consisting of lubricants, gels, creams, and combinations thereof. In some embodiments, the interfering substance comprises a gel comprising one or more carbomers. In some embodiments, the interfering substance comprises a gel that does not comprise any carbomers.

Also disclosed herein is a method of maintaining or enhancing performance of diagnostic testing of a sample in presence of interfering substance(s). In some embodiments, the method comprises transferring the sample into a buffer composition as described above in the "Buffer Compositions" section or described elsewhere herein. In some embodiments, the method further comprises, preceding to the transferring step, collecting the sample on a swab from a subject. In some embodiments, the method further comprises, subsequent to the transferring step, amplifying and detecting one or more nucleic acids in the biological sample or amplifying and detecting one or more nucleic acids extracted from the biological sample.

In some embodiments, the performance comprises sensitivity, specificity, recall, accuracy, promptness, robustness, or a combination thereof.

In some embodiments, the method reduces the incidence of non-reportable results by, or by about, or by at least, or by at least about, or by at most, or by at most about, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%, or a range between any two of these values. In some embodiments, the method reduces the incidence of non-reportable results by at least 5%, at least 10%, at least 20%, at least 30%, at least 40%, at least 50%, at least 60%, at least 70%, at least 80%, or at least 90%. In some embodiments, the non-reportable results comprise indeterminate results, unresolved results, incomplete results, or a combination thereof.

In some embodiments, the method maintains, or maintains about, or maintains at least, or maintains at least about, or maintains at most, or maintains at most about, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95% accuracy rate, or a range between any two of these values. In some embodiments, the method maintains at least 90%, at least 95%, at least 98%, or at least 99% accuracy rate. In some embodiments, the accuracy rate is measured by an agreement rate of positive results, an agreement rate of negative results, an overall rate of agreement, or a combination thereof.

EXAMPLES

The following examples are provided to demonstrate particular situations and settings in which this technology can be applied and are not intended to restrict the scope of the invention and the claims included in this disclosure.

Example 1

Diagnostic Assays Performed on Vaginal Samples

The studies described herein this section illustrate the robust performance of diagnostic assays achieved by use of the buffer compositions disclosed herein this application for detecting vaginal disorders, for example, vulvovaginal candidiasis (VVC), trichomoniasis and bacterial vaginosis (BV), in clinical vaginal-swab samples that can contain interfering substances. For example, the assays implemented fully automated in vitro diagnostic tests on the BD MAX™ system for qualitative detection of *Candida* spp. (e.g., *C. glabrata* and *C. krusei*), *T. vaginalis* and/or BV-related bacteria. The assays incorporated microfluidic-based sample processing and nucleic acid-based detection methods. More specifically, the diagnostic assays utilized fluidically-operated magnetic particles for nucleic acid extraction, real-time polymerase chain reaction (PCR) for amplification of target DNAs, and fluorogenic hybridization probes for identification of target organisms.

The diagnostic assays, as discussed below in Examples 2 to 9 and 11, were carried out using either Example Buffer I or II. In comparison, diagnostic assays were also carried out using Comparative Buffer. The compositions of Comparative Buffer, Example Buffer I, and Example Buffer II are summarized below in Table 1. The Comparative Buffer of Table 1 represents the prevalent "gold standard" buffer composition as used in biological sample preparations and diagnostic detections for vaginal disorders or sexually transmitted diseases.

TABLE 1

Buffer Compositions

| Component | Comparative Buffer | Example Buffer I | Example Buffer II |
|---|---|---|---|
| Acid-base pair | 436.5 mM $KH_2PO_4$ 48.5 mM $K_2HPO_4$ | 105 mM acetic acid 395 mM $CH_3COONa$ | 105 mM acetic acid 395 mM $CH_3COONa$ |
| Chelating agent | 10 mM EDTA | 10 mM EDTA | 10 mM EDTA |
| Surfactant | — | 1% Tergitol ™ 15-S-9 | 0.5% Triton X-100 |
| Divalent salt | — | 200 mM $CaCl_2$ | 200 mM $CaCl_2$ |
| pH range | 5.6 to 5.8 | (approximately 5.0) | (approximately 5.0) |
| Biocidal preservative | 0.03% ProClin ™ 300 | 0.03% ProClin ™ 300 | 0.03% ProClin ™ 300 |

The use of potassium phosphate monobasic ($KH_2PO_4$)/potassium phosphate dibasic ($K_2HPO_4$) as an acid-base pair in the Comparative Buffer was found to be associated with greater particle aggregation and more frequent microfluidic clogging than the use of acetic acid/sodium acetate ($CH_3COONa$) in the Example Buffers. The inclusions of surfactant (e.g., Tergitol™ 15-S-9 or Triton X-100) and salt (e.g., $CaCl_2$) in the Example Buffers were found to improve robustness of assay performance by reducing interactions of the magnetic particles with polyelectrolytes (e.g., carbomers) commonly present in interfering gels. The presence of ethylenediaminetetraacetic acid (EDTA), as an chelating agent, in all three buffer compositions was found essential for sample stabilization. ProClin™ 300 preservative (Sigma Aldrich, St. Louis, Mo.) was added in all three buffer compositions as a biocidal agent for sample preservation purposes.

Vaginal swabs were collected from a total of 263 women with clinical symptoms of vaginitis or/and vaginosis and tested on the BD MAX™ System. FIG. 1 summarizes the composition of these sample donors by geographical region: 94 donors (36%) from Biocollection Oakland, 69 donors (26%) from PPGC Houston, and 100 donors (38%) from Biocollection Miami.

This example illustrates the experimental aspects of the diagnostic assays, of which the results are discussed below in Examples 2 to 9. In particular, this example illustrates exemplary buffer compositions as disclosed herein this application.

Example 2

Test Repeatability

Table 2 summarizes the agreement rates between the assay results obtained in two tests ("first take" and "second take") of the same sample ("same swab"). The Comparative Buffer was used in the assays of Table 2(a), and the Example Buffer I in those of Table 2(b). Listed in each of Tables 2(a)-2(b) are the agreement rates of the positive results, the negative results, and overall (from left to right) for *Candida* spp., *C. glabrata, C. krusei, T. vaginalis*, and BV (from top to bottom).

Table 2. Baseline Repeatability of the Diagnostic Assays

2(a).

| | Agreement Rates (%) | | |
|---|---|---|---|
| Pathogenic Markers | Positive Results | Negative Results | Overall |
| *Candida spp.* | 93.9 | 97.3 | 96.5 |
| *C. glabrata* | 91.7 | 100.0 | 99.6 |
| *C. krusei* | 100.0 | 100.0 | 100.0 |
| *T. vaginalis* | 97.1 | 100.0 | 99.6 |
| BV | 97.6 | 98.2 | 97.9 |

2(b).

| | Agreement Rates (%) | | |
|---|---|---|---|
| Pathogenic Markers | Positive Results | Negative Results | Overall |
| *Candida spp.* | 93.6 | 97.9 | 97.0 |
| *C. glabrata* | 90.0 | 99.6 | 99.2 |
| *C. krusei* | 100.0 | 100.0 | 100.0 |
| *T. vaginalis* | 97.1 | 99.5 | 99.2 |
| BV | 99.2 | 98.2 | 98.8 |

Both the Comparative Buffer and the Example Buffer I achieved at least 90.0% agreement between two different tests ("first take" and "second take") of the "same swab," when diagnostic detections for various pathogenic markers were performed.

As such, this example provides a representative baseline for the repeatability of the diagnostic assay and related methods.

Example 3

Test Reproducibility

Table 3 summarizes the agreement rates between the assay results obtained, respectively, in a test ("first take") of one of the two samples ("swab 1" and "swab 2") collected from the same subject (or sample donor). The Comparative Buffer was used in the assays of Table 3(a), and the Example Buffer I in those of Table 3(b). Listed in each of Tables 3(a)-3(b) are the agreement rates of the positive results, the negative results, and overall (from left to right) for *Candida* spp., *C. glabrata, C. krusei, T. vaginalis*, and BV (from top to bottom).

Both the Comparative Buffer and the Example Buffer I achieved at least 90.0% agreement between two different samples ("swab 1" and "swab 2") obtained from the same subject, when various pathogenic markers were tested.

Table 3. Baseline Reproducibility of the PCR Assay for Pathogen Detections

3(b).

| | Agreement Rates (%) | | |
|---|---|---|---|
| Pathogenic Markers | Positive Results | Negative Results | Overall |
| *Candida spp.* | 97.9 | 97.9 | 97.9 |
| *C. glabrata* | 90.0 | 99.1 | 98.7 |
| *C. krusei* | 100.0 | 100.0 | 100.0 |
| *T. vaginalis* | 94.4 | 99.5 | 98.7 |
| BV | 98.4 | 94.7 | 96.7 |

3(a).

| | Agreement Rates (%) | | |
|---|---|---|---|
| Pathogenic Markers | Positive Results | Negative Results | Overall |
| *Candida spp.* | 98.0 | 96.6 | 96.9 |
| *C. glabrata* | 100.0 | 100.0 | 100.0 |
| *C. krusei* | 100.0 | 100.0 | 100.0 |
| *T. vaginalis* | 100.0 | 99.5 | 99.6 |
| BV | 93.5 | 95.3 | 94.4 |

As such, this example demonstrates a representative baseline for the reproducibility of the diagnostic assay and related methods.

Example 4

Baseline Effects of Buffer on Reportable Results

Table 4 illustrates the buffer-dependent variance in the reported assay results for five sets of representative biomarkers: *Candida* spp. (Table 4(a)), *C. glabrata* (Table 4(b)), *C. krusei* (Table 4(c)), *T. vaginalis* (Table 4(d)), and bacterial vaginosis (BV) (Table 4(e)).

For example, as shown in Table 4(a), when the Example Buffer was used in the assay, the PCR analysis reported 45 positive and 178 negative results for *Candida* spp.; while, when the Comparative Buffer was used, the PCR analysis reported 46 positive and 177 negative results for *Candida* spp. Among the 223 results reported in Table 4(a), three samples (upper right), reported as negative in the Comparative Buffer, were identified as pathogenic-positive in the Example Buffer; and four samples (bottom left), reported as positive in the Comparative Buffer, were identified as pathogenic-negative in the Example Buffer.

Table 4. Difference in Results Reported Using Example Buffer and Comparative Buffer 4(a). Detection of *Candida* spp.

| | | In Comparative Buffer | |
|---|---|---|---|
| | | Positive (+) results | Negative (−) results |
| In Example Buffer | Positive (+) results | 42 | 3 |
| | Negative (−) results | 4 | 174 |

4(c). Detection of *C. krusei*

| | | In Comparative Buffer | |
|---|---|---|---|
| | | Positive (+) results | Negative (−) results |
| In Example Buffer | Positive (+) results | 0 | 0 |
| | Negative (−) results | 0 | 223 |

4(d). Detection of *T. vaginalis*

| | | In Comparative Buffer | |
|---|---|---|---|
| | | Positive (+) results | Negative (−) results |
| In Example Buffer | Positive (+) results | 35 | 1 |
| | Negative (−) results | 1 | 186 |

4(b). Detection of *C. glabrata*

| | | In Comparative Buffer | |
|---|---|---|---|
| | | Positive (+) results | Negative (−) results |
| In Example Buffer | Positive (+) results | 11 | 0 |
| | Negative (−) results | 2 | 210 |

As an example, as shown in Table 4(b), when the Example Buffer was used in the assay, the PCR analysis reported 11 positive and 212 negative results for *C. glabrata*; while, when the Comparative Buffer was used, the PCR analysis reported 13 positive and 210 negative results for *C. glabrata*. Among the 223 results reported in Table 4(b), two samples (bottom left), reported as positive in the Comparative Buffer, were identified as pathogenic-negative in the Example Buffer.

4(e). Detection of BV

| | | In Comparative Buffer | |
|---|---|---|---|
| | | Positive (+) results | Negative (−) results |
| In Example Buffer | Positive (+) results | 122 | 7 |
| | Negative (−) results | 7 | 97 |

As an example, as shown in Table 4(c), when the Example Buffer was used in the assay, the PCR analysis reported 0 positive and 223 negative results for *C. krusei*; while, when the Comparative Buffer was used, the PCR analysis reported 0 positive and 223 negative results for *C. krusei*.

As an example, as shown in Table 4(d), when the Example Buffer was used in the assay, the PCR analysis reported 36 positive and 187 negative results for *T. vaginalis*; while, when the Comparative Buffer was used, the PCR analysis reported 36 positive and 187 negative results for *T. vaginalis*. Among the 223 results reported in Table 4(d), one sample (upper right), reported as negative in the Comparative Buffer, was identified as pathogenic-positive in the Example Buffer; and one sample (bottom left), reported as positive in the Comparative Buffer, was identified as pathogenic-negative in the Example Buffer.

As an example, as shown in Table 4(e), when the Example Buffer was used in the assay, the PCR analysis reported 129 positive and 104 negative results for BV; while, when the Comparative Buffer was used, the PCR analysis reported 129 positive and 104 negative results for *C. glabrata*. Among the 233 reportable results in Table 4(e), seven samples (upper right), reported as negative in the Comparative Buffer, were identified as pathogenic-positive in the Example Buffer; and seven samples (bottom left), reported as positive in the Comparative Buffer, were identified as pathogenic-negative in the Example Buffer.

Table 5 summarizes the agreement rates of the assay results (generally greater than 84%), as shown in Table 4, between the Example Buffer and Comparative Buffer. In particular, the agreement rates of the positive results, the negative results, and overall (from left to right) were tested for *Candida* spp., *C. glabrata, C. krusei, T. vaginalis*, and BV (from top to bottom).

This example illustrates representative baselines for evaluating effects of the assay buffer on reportable results of the diagnostic assay and related methods.

TABLE 5

Agreement (%) between the assay results obtained using Example Buffer I and Comparative Buffer

| Pathogenic Marker | Agreement Rates (%) Positive Results | Negative Results | Overall |
|---|---|---|---|
| *Candida* spp. | 91.3 | 98.3 | 96.9 |
| *C. glabrata* | 84.6 | 100.0 | 99.1 |
| *C. krusei* | 100.0 | 100.0 | 100.0 |
| *T. vaginalis* | 97.2 | 99.5 | 99.1 |
| BV | 94.6 | 93.3 | 94.0 |

Example 5

Baseline Effects of Buffer on Non-Reportable Results

Tables 6-7 illustrate the non-reportable rates when the Comparative Buffer (Tables 6(a)-6(d), 7(a)-7(f)) and the Example Buffer I (Tables 6(e)-6(h), 7(g)-7(1)) were used, respectively, in the assay tests for vaginal disorders. The samples examined in Table 6 did not contain interfering gels, while those examined in Table 7 contained various interfering gels, including McKesson lubricating jelly (Tables 7(a), 7(g)), E-Z lubricating jelly (Tables 7(b), 7(h)), Surgilube® lubricant (Tables 7(c), 7(i)), Canesten® (clotrimazole antifungal cream) (Tables 7(d), 7(j)), and Vagisil® (benzocaine/resorcinol anti-itching cream) (Tables 7(e), 7(k)). Each of the swab samples examined in Tables 6-7 was assayed for both vaginitis and vaginosis, and the non-reportable rates listed in Tables 6-7 were further broken down into the rates of unresolved results and indeterminate results.

With respect to the assay tests of swab samples without interfering gels, Tables 6(a) and 6(e) compare the first tests of a sample ("swab 1, take 1") performed by using the Comparative Buffer and the Example Buffer I, respectively; Tables 6(b) and 6(f) compare the second tests of a sample ("swab 1, take 2") performed by using the two buffers; Tables 6(c) and 6(g) compare the first tests of a second sample ("swab 2, take 1"); and Tables 6(d) and 6(h) compare the overall results, respectively, as obtained from the tests of Tables 6(a)-6(c) and 6(e)-6(g).

Table 6. Non-Reportable Rates from Samples without Interfering Substance Remain Comparable Between the Comparative Buffer and the Example Buffer 6(a)-6(d). 6(e)-6(h)

Assays Using Comparative Buffer Assays Using Example Buffer I

TABLE 6(a)

| Test 1 of Sample 1 | | | |
|---|---|---|---|
| | Un-resolved (%) | Indeter-minate (%) | Non-reportable (%) |
| Vaginitis | 5.0 | 2.3 | 7.3 |
| Vaginosis | 4.2 | 2.3 | 6.5 |
| Per sample | 6.9 | 2.3 | 9.2 |

TABLE 6(e)

| Test 1 of Sample 1 | | | |
|---|---|---|---|
| | Un-resolved (%) | Indeter-minate (%) | Non-reportable (%) |
| Vaginitis | 4.6 | 2.3 | 6.9 |
| Vaginosis | 1.9 | 2.3 | 4.2 |
| Per sample | 6.2 | 2.3 | 8.5 |

TABLE 6(b)

| Test 2 of Sample 1 | | | |
|---|---|---|---|
| | Un-resolved (%) | Indeter-minate (%) | Non-reportable (%) |
| Vaginitis | 3.9 | 2.3 | 6.2 |
| Vaginosis | 3.9 | 2.3 | 6.2 |
| Per sample | 6.5 | 2.3 | 8.9 |

TABLE 6(f)

| Test 2 of Sample 1 | | | |
|---|---|---|---|
| | Un-resolved (%) | Indeter-minate (%) | Non-reportable (%) |
| Vaginitis | 2.7 | 1.9 | 4.6 |
| Vaginosis | 1.9 | 1.9 | 3.9 |
| Per sample | 3.9 | 1.9 | 5.8 |

TABLE 6(c)

| Test 1 of Sample 2 | | | |
|---|---|---|---|
| | Un-resolved (%) | Indeter-minate (%) | Non-reportable (%) |
| Vaginitis | 3.1 | 2.3 | 5.4 |
| Vaginosis | 4.6 | 2.3 | 6.9 |
| Per sample | 6.2 | 2.3 | 8.5 |

TABLE 6(g)

| Test 1 of Sample 2 | | | |
|---|---|---|---|
| | Un-resolved (%) | Indeter-minate (%) | Non-reportable (%) |
| Vaginitis | 2.7 | 1.9 | 4.6 |
| Vaginosis | 1.9 | 1.9 | 3.9 |
| Per sample | 3.5 | 1.9 | 5.4 |

TABLE 6(d)

| Overall | | | |
|---|---|---|---|
| | Un-resolved (%) | Indeter-minate (%) | Non-reportable (%) |
| Vaginitis | 4.0 | 2.3 | 6.3 |
| Vaginosis | 4.2 | 2.3 | 6.5 |
| Per sample | 6.5 | 2.3 | 8.9 |

TABLE 6(h)

| Overall | | | |
|---|---|---|---|
| | Un-resolved (%) | Indeter-minate (%) | Non-reportable (%) |
| Vaginitis | 3.3 | 2.1 | 5.4 |
| Vaginosis | 1.9 | 2.1 | 4.0 |
| Per sample | 4.5 | 2.1 | 6.5 |

Table 7. Example Buffer Reduces Non-Reportable Rates when Samples Contain Interfering Substances (Lubricants)

7(a)-7(c). 7(g)-7(i)

Assays Using Comparative Buffer Assays Using Example Buffer I

| 7(a). McKesson | | | |
|---|---|---|---|
| | Un-resolved (%) | Indeter-minate (%) | Non-reportable (%) |
| Vaginitis | 21.7 | 34.8 | 56.5 (13/23) |
| Vaginosis | 26.1 | 34.8 | 60.9 (14/23) |
| Per sample | 34.8 | 34.8 | 69.6 (16/23) |

| 7(g). McKesson | | | |
|---|---|---|---|
| | Un-resolved (%) | Indeter-minate (%) | Non-reportable (%) |
| Vaginitis | 0.0 | 0.0 | 0.0 (0/23) |
| Vaginosis | 8.7 | 0.0 | 8.7 (2/23) |
| Per sample | 8.7 | 0.0 | 8.7 (2/23) |

| 7(b). E-Z (Medline Industries, mc) | | | |
|---|---|---|---|
| | Un-resolved (%) | Indeter-minate (%) | Non-reportable (%) |
| Vaginitis | 23.1 | 53.8 | 76.9 (20/26) |
| Vaginosis | 7.7 | 53.8 | 61.5 (16/26) |
| Per sample | 23.1 | 53.8 | 76.9 (20/26) |

| 7(h). E-Z (Medline Industries, Inc.) | | | |
|---|---|---|---|
| | Un-resolved (%) | Indeter-minate (%) | Non-reportable (%) |
| Vaginitis | 0.0 | 0.0 | 0.0 (0/26) |
| Vaginosis | 0.0 | 0.0 | 0.0 (0/26) |
| Per sample | 0.0 | 0.0 | 0.0 (0/26) |

| 7(c). Surgilube ® | | | |
|---|---|---|---|
| | Un-resolved (%) | Indeter-minate (%) | Non-reportable (%) |
| Vaginitis | 50.0 | 0.0 | 50.0 (12/24) |
| Vaginosis | 16.7 | 0.0 | 16.7 (4/24) |
| Per sample | 50.0 | 0.0 | 50.0 (12/24) |

| 7(i). Surgilube ® | | | |
|---|---|---|---|
| | Un-resolved (%) | Indeter-minate (%) | Non-reportable (%) |
| Vaginitis | 0.0 | 0.0 | 0.0 (0/24) |
| Vaginosis | 0.0 | 0.0 | 0.0 (0/24) |
| Per sample | 0.0 | 0.0 | 0.0 (0/24) |

Table 7. Example Buffer Reduces Non-Reportable Rates when Samples Contain Interfering Substances (Continued)

7(d)-7(f). 7(j)-7(l)

Assays Using Comparative Buffer Assays Using Example Buffer I

| 7(d). Canesten ® | | | |
|---|---|---|---|
| | Un-resolved (%) | Indeter-minate (%) | Non-reportable (%) |
| Vaginitis | 69.6 | 0.0 | 69.6 (16/23) |
| Vaginosis | 4.3 | 0.0 | 4.3 (1/23) |
| Per sample | 73.9 | 0.0 | 73.9 (17/23) |

7(j). Canesten ®

| | Un-resolved (%) | Indeter-minate (%) | Non-reportable (%) |
|---|---|---|---|
| Vaginitis | 13.0 | 0.0 | 13.0 (3/23) |
| Vaginosis | 0.0 | 0.0 | 0.0 (0/23) |
| Per sample | 13.0 | 0.0 | 13.0 (3/23) |

7(e). Vagisil ®

| | Un-resolved (%) | Indeter-minate (%) | Non-reportable (%) |
|---|---|---|---|
| Vaginitis | 60.9 | 17.4 | 78.3 (18/23) |
| Vaginosis | 8.7 | 17.4 | 23.1 (6/23) |
| Per sample | 65.2 | 17.4 | 82.6 (19/23) |

7(k). Vagisil ®

| | Un-resolved (%) | Indeter-minate (%) | Non-reportable (%) |
|---|---|---|---|
| Vaginitis | 43.5 | 0.0 | 43.5 (10/23) |
| Vaginosis | 39.1 | 0.0 | 39.1 (9/23)) |
| Per sample | 43.5 | 0.0 | 43.5 (10/23) |

7(f). Overall

| | Un-resolved (%) | Indeter-minate (%) | Non-reportable (%) |
|---|---|---|---|
| Vaginitis | 44.5 | 21.9 | 66.4 (79/119) |
| Vaginosis | 12.7 | 21.9 | 34.5 (41/119) |
| Per sample | 47.1 | 21.8 | 68.9 (82/119) |

7(l). Overall

| | Un-resolved (%) | Indeter-minate (%) | Non-reportable (%) |
|---|---|---|---|
| Vaginitis | 10.9 | 0.0 | 10.9 (13/119) |
| Vaginosis | 9.2 | 0.0 | 9.2 (11/119) |
| Per sample | 12.6 | 0.0 | 12.6 (15/119) |

As shown in Table 6, the Example Buffer I and the Comparative Buffer yielded comparable non-reportable rates when the assays were not interfered with gels.

Accordingly, use of the Example Buffer I was demonstrated to maintain the level of reportable results for samples without interfering gels.

As shown in Table 7, the Example Buffer I significantly reduced the non-reportable rates when the swab samples contained interfering substances. For example, for the swab samples contaminated with McKesson lubricating jelly, the use of the Example Buffer I reduced the un-resolved, indeterminate, and total non-reportable rates per sample from 34.8%, 34.8%, and 69.6% (Table 7(a)) to 8.7%, 0.0%, and 8.7% (Table 7(g)). As another example, for the swab samples contaminated with E-Z lubricating jelly, the use of the Example Buffer I reduced the un-resolved, indeterminate, and total non-reportable rates per sample from 23.1%, 53.8%, and 76.9% (Table 7(b)) to 0.0%, 0.0%, and 0.0% (Table 7(h)).

Overall, the un-resolved, indeterminate, total non-reportable rates per sample were reduced from 47.1%, 21.8%, and 68.9% (Table 7(f)) to 12.6%, 0.0%, and 12.6% (Table 7(1)).

As such, this example illustrates that use of the Example Buffer can significantly improve the assay performance by enhancing the test robustness against presence of various interfering substances, while still maintaining the reportable rates at a level absent interfering substances.

Example 6

Robustness of Comparative Buffer to Interference

Diagnostic assays were performed on 119 clinical swab samples using the Comparative Buffer. Among these 119 samples, only 37 (about 31.1%) yielded reportable results. For each of these 119 samples, a test ("Take 1") was run in the absence of interfering gels, and another test ("Take 2") was run in the presence of interfering gels.

Table 8 illustrates the effects of the presence of interfering gels on the reportable assay results for detecting *Candida* spp. (Table 8(a)), *C. glabrata* (Table 8(b)), *C. krusei* (Table 8(c)), *T. vaginalis* (Table 8(d)), and bacterial vaginosis (BV) (Table 8(e)).

For example, as shown in Table 8(e), in the presence of interfering gels, the diagnostic assays reported 34 positive and 37 negative results for BV; while in the absence of interfering gels, the diagnostic assays reported 38 positive and 33 negative results for BV. Among the results reported in Table 8(d), two samples (upper right), reported as positive in the presence of interfering gels, were identified as negative in the absence of interfering gels; and six samples (bottom left), reported as negative in the presence of interfering gels, were identified as positive in the absence of interfering gels.

Table 8. Reported Assay Results Using the Comparative Buffer

8(a). Detection of *Candida* spp.

| | | In absence of interfering gel | |
|---|---|---|---|
| | | Positive (+) results | Negative (−) results |
| In presence of interfering gel | Positive (+) results | 6 | 0 |
| | Negative (−) results | 1 | 30 |

8(c). Detection of *T. vaginalis*

| | | In absence of interfering gel | |
|---|---|---|---|
| | | Positive (+) results | Negative (−) results |
| In presence of interfering gel | Positive (+) results | 10 | 0 |
| | Negative (−) results | 0 | 27 |

8(b). Detection of *C. glabrata*

| | | In absence of interfering gel | |
|---|---|---|---|
| | | Positive (+) results | Negative (−) results |
| In presence of interfering gel | Positive (+) results | 5 | 0 |
| | Negative (−) results | 0 | 32 |

8(d). Detection of BV

| | | In absence of interfering gel | |
|---|---|---|---|
| | | Positive (+) results | Negative (−) results |
| In presence of interfering gel | Positive (+) results | 32 | 2 |
| | Negative (−) results | 6 | 31 |

Table 9 summarizes the agreement rates (generally greater than 84%) of the assay results, as shown in Table 8, between tests in the presence and absence of interfering gels. In particular, the agreement rates of the positive results, the negative results, and overall (from left to right) were tested for *Candida* spp., *C. glabrata, C. krusei, T. vaginalis*, and BV (from top to bottom).

TABLE 9

Assay robustness against interfering substance in samples, measured by agreement (%) between positive, negative and overall results

| Pathogenic markers | Agreement rates (%) Positive results | Negative results | Overall |
|---|---|---|---|
| *Candida* spp. | 85.7 | 100.0 | 97.3 |
| *C. glabrata* | 100.0 | 100.0 | 100.0 |
| *C. krusei* | 100.0 | 100.0 | 100.0 |
| *T. vaginalis* | 100.0 | 100.0 | 100.0 |
| BV | 84.2 | 93.9 | 88.7 |

This example illustrates the limited assay performance, particularly the low reportable rates, when the Comparative Buffer was used.

Example 7

Robustness of Example Buffer to Interference

Diagnostic assays were performed on 119 clinical swab samples using the Example Buffer I. Among these 119 samples, 104 (about 87.4%) yielded reportable results, as opposed to about 31.1% in Example 6. Accordingly, as compared with the use of the Comparative Buffer in Example 6, the use of the Example Buffer I significantly increased the reportable rates of the diagnostic assays. For each of these 119 samples, a test ("Take 1") was run in the absence of interfering gels, and another test ("Take 2") was run in the presence of interfering gels.

Similar to Table 8 of Example 6, Table 10 illustrates the effects of the presence of interfering gels on the reportable assay results for detecting *Candida* spp. (Table 10(a)), *C. glabrata* (Table 10(b)), *C. krusei* (Table 10(c)), *T. vaginalis* (Table 10(d)), and bacterial vaginosis (BV) (Table 10(e)) when the Example Buffer I was utilized.

For example, as shown in Table 10(d), in the presence of interfering gels, the diagnostic assays reported 54 positive and 50 negative results for BV; while in the absence of interfering gels, the diagnostic assays reported 55 positive and 49 negative results for BV. Among these reported results in Table 10(d), one sample (upper right), reported as positive in the presence of interfering gels, was identified as negative in the absence of interfering gels; and two samples (bottom left), reported as negative in the presence of interfering gels, were identified as positive in the absence of interfering gels.

Table 10. Reported Assay Results Using the Example Buffer I

10(a). Detection of *Candida* spp.

| | | In absence of interfering gel | |
|---|---|---|---|
| | | Positive (+) results | Negative (−) results |
| In presence of interfering gel | Positive (+) results | 14 | 1 |
| | Negative (−) results | 2 | 83 |

| 10(c). Detection of *T. vaginalis* | | | |
|---|---|---|---|
| | | In absence of interfering gel | |
| | | Positive (+) results | Negative (−) results |
| In presence of interfering gel | Positive (+) results | 14 | 0 |
| | Negative (−) results | 1 | 85 |

| 10(b). Detection of *C. glabrata* | | | |
|---|---|---|---|
| | | In absence of interfering gel | |
| | | Positive (+) results | Negative (−) results |
| In presence of interfering gel | Positive (+) results | 5 | 1 |
| | Negative (−) results | 0 | 94 |

| 10(d). Detection of BV | | | |
|---|---|---|---|
| | | In absence of interfering gel | |
| | | Positive (+) results | Negative (−) results |
| In presence of interfering gel | Positive (+) results | 53 | 1 |
| | Negative (−) results | 2 | 48 |

TABLE 11

Assay robustness against interfering substance in samples, measured by agreement (%) between positive, negative and overall results

| Pathogenic | Agreement rates (%) | | |
|---|---|---|---|
| markers | Positive results | Negative results | Overall |
| *Candida* spp. | 87.5 | 98.8 | 97.0 |
| *C. glabrata* | 100.0 | 99.0 | 99.0 |
| *C. krusei* | 100.0 | 100.0 | 100.0 |
| *T. vaginalis* | 93.3 | 100.0 | 99.0 |
| BV | 96.4 | 98.0 | 97.1 |

Table 11 summarizes the agreement rates (generally greater than 87%) of the assay results, as shown in Table 10, between tests in the presence and absence of interfering gels. In particular, the agreement rates of the positive results, the negative results, and overall (from left to right) were tested for *Candida* spp., *C. glabrata, C. krusei, T. vaginalis*, and BV (from top to bottom).

The agreement rates as shown in Table 11 are at least comparable to those as shown in Table 9. As such, the use of the Example Buffer I (Tables 10-11) was demonstrated to maintain the same accuracy level as the use of the Comparative Buffer (Tables 8-9).

Accordingly, this example illustrates that the use of the Example Buffer increases the reportable rates without affecting the reproducibility of the diagnostic assays under noise conditions.

Example 8

Example Buffer Prevents/Reduces Microfluidic Clogging

Figures 2, 2A, 2B:
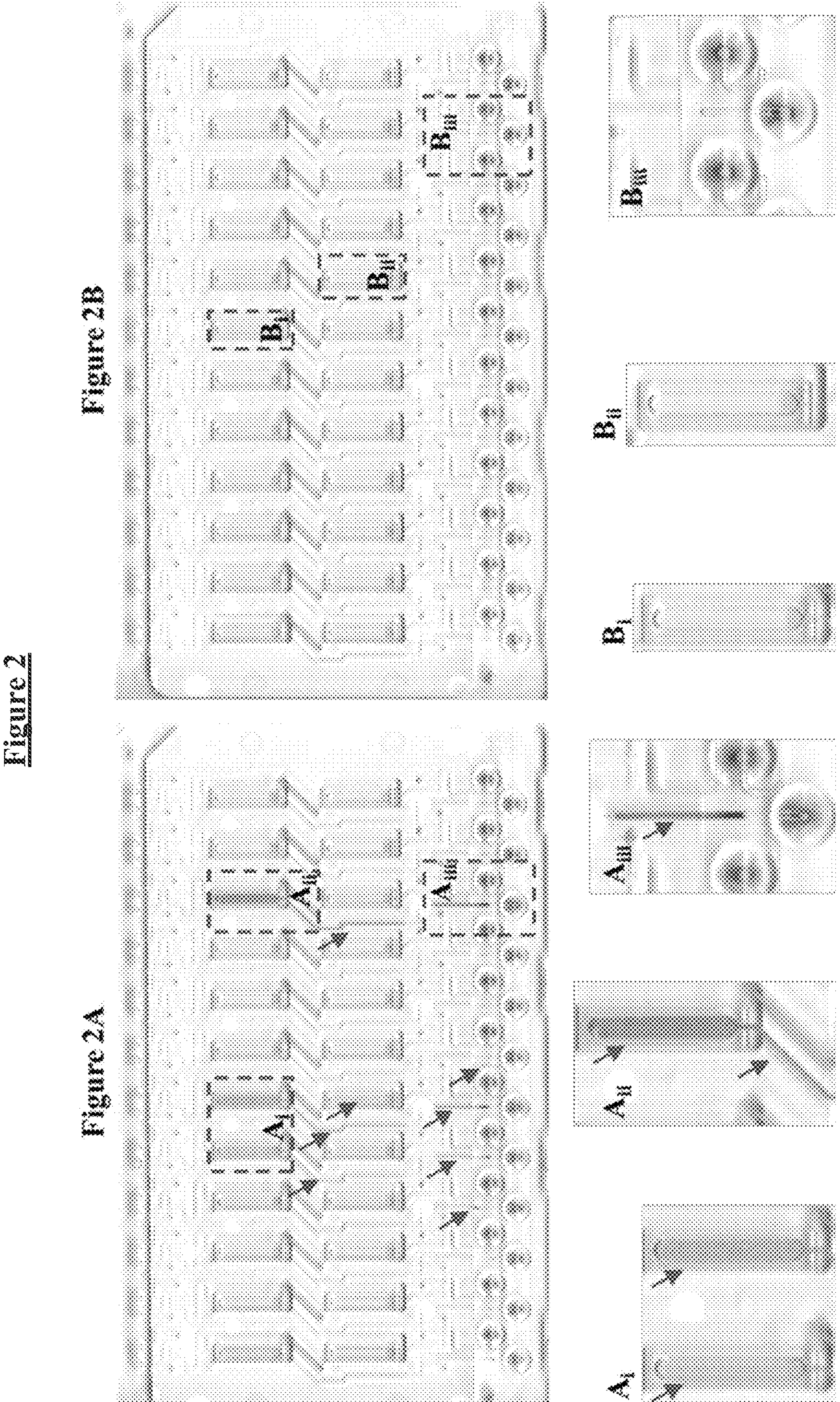

FIGS. 2A-2B show photographs of BD MAX™ PCR cartridges, each of which has been utilized in a diagnostic testing of a clinical vaginal-swab sample that does not contain interfering gels. The Example Buffer I was utilized in the testing of FIG. 2A, and the Comparative Buffer was utilized in the testing of FIG. 2B. As indicated by red arrows in FIG. 2A, magnetic particles, deployed in the cartridge for nucleic acid extraction, formed aggregates when the diagnostic assay was performed using the Comparative Buffer. The particle aggregation resulted in microfluidic clogging as shown in FIG. 2A. Exemplary areas of particle aggregation and microfluidic clogging in FIG. 2A are marked as "$A_i$," "$A_{ii}$," and "$A_{iii}$" and enlarged at the bottom. In comparison, no such particle aggregation or microfluidic clogging was observed in FIG. 2B, and exemplary areas of FIG. 2B are marked as "$B_i$," "$B_{ii}$," and "$B_{iii}$" and enlarged at the bottom.

Figures 3, 3A, 3B:
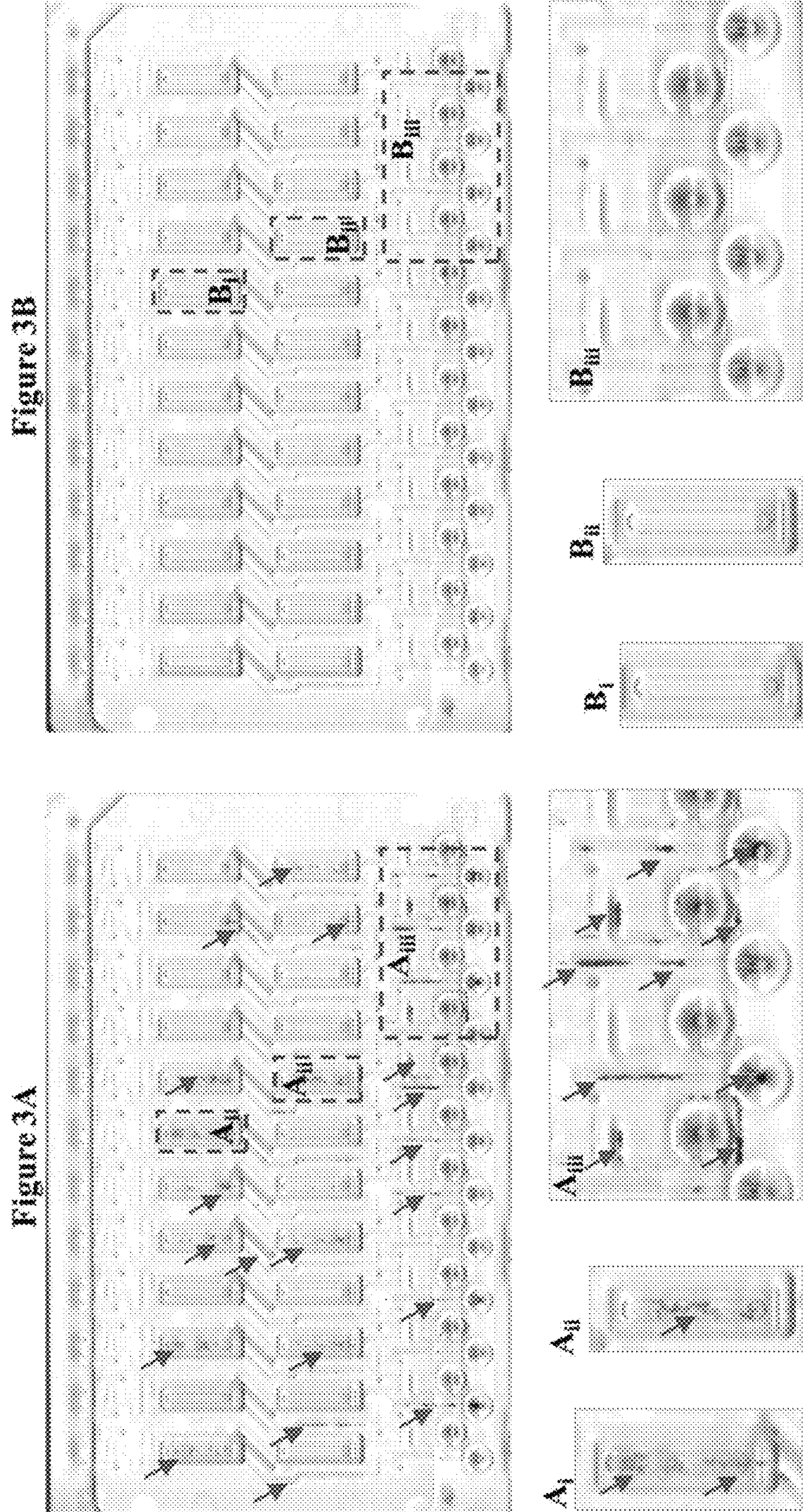
Figures 4, 4A, 4B:
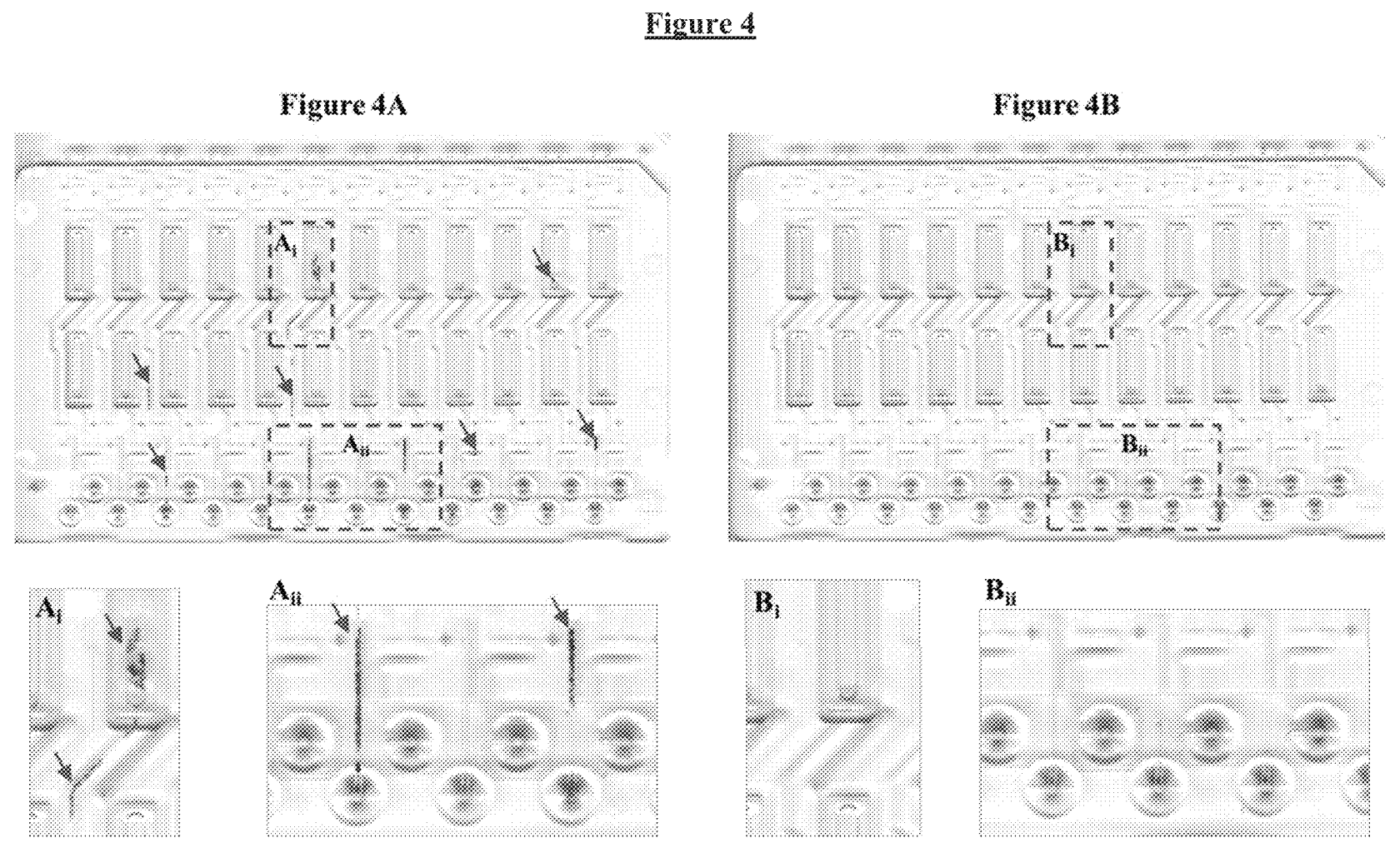

FIGS. 3A-3B show photographs of BD MAX™ PCR cartridges, each of which has been utilized in a diagnostic testing of a clinical vaginal-swab sample that contains a carbomer-based interfering gel, McKesson. FIGS. 4A-4B show additional embodiments of photographs of BD MAX™ PCR cartridges utilized in testing an additional interfering gel E-Z brand (Medline Industries, Inc.) (FIGS. 4A-4B) present at 10 μL.

As indicated by red arrows in FIGS. 3A and 4A, magnetic particles, deployed in the cartridge for nucleic acid extraction, formed aggregates when the diagnostic assay was performed using the Comparative Buffer. The particle aggregation then resulted in microfluidic clogging, as shown in FIGS. 3A and 4A. Exemplary areas of particle aggregation and microfluidic clogging in FIG. 3A are marked as "$A_i$," "$A_{ii}$," and "$A_{iii}$" and enlarged at the bottom. Exemplary areas of particle aggregation and microfluidic clogging in FIG. 4A are marked as "$A_i$," "$A_{ii}$," and "$A_{iii}$" and enlarged at the bottom. In comparison, no such particle aggregation or microfluidic clogging were observed in FIG. 3B, for example, at areas marked as "$B_i$," "$B_{ii}$," and "$B_{iii}$" and enlarged at the bottom. Nor were any particle aggregation or microfluidic clogging observed in FIG. 4B, for example, at areas marked as "$B_i$," and "$B_{ii}$," and enlarged at the bottom.

As such, this example illustrates that the use of the buffer composition disclosed herein this application prevents or reduces particle aggregation and microfluidic clogging in the BD MAX™ PCR cartridges during diagnostic assays.

Example 9

Example Buffer Improves/Maintains Diagnostic Accuracy

Figures 5, 5A, 5B, 5C, 5D, 5E, 5F:
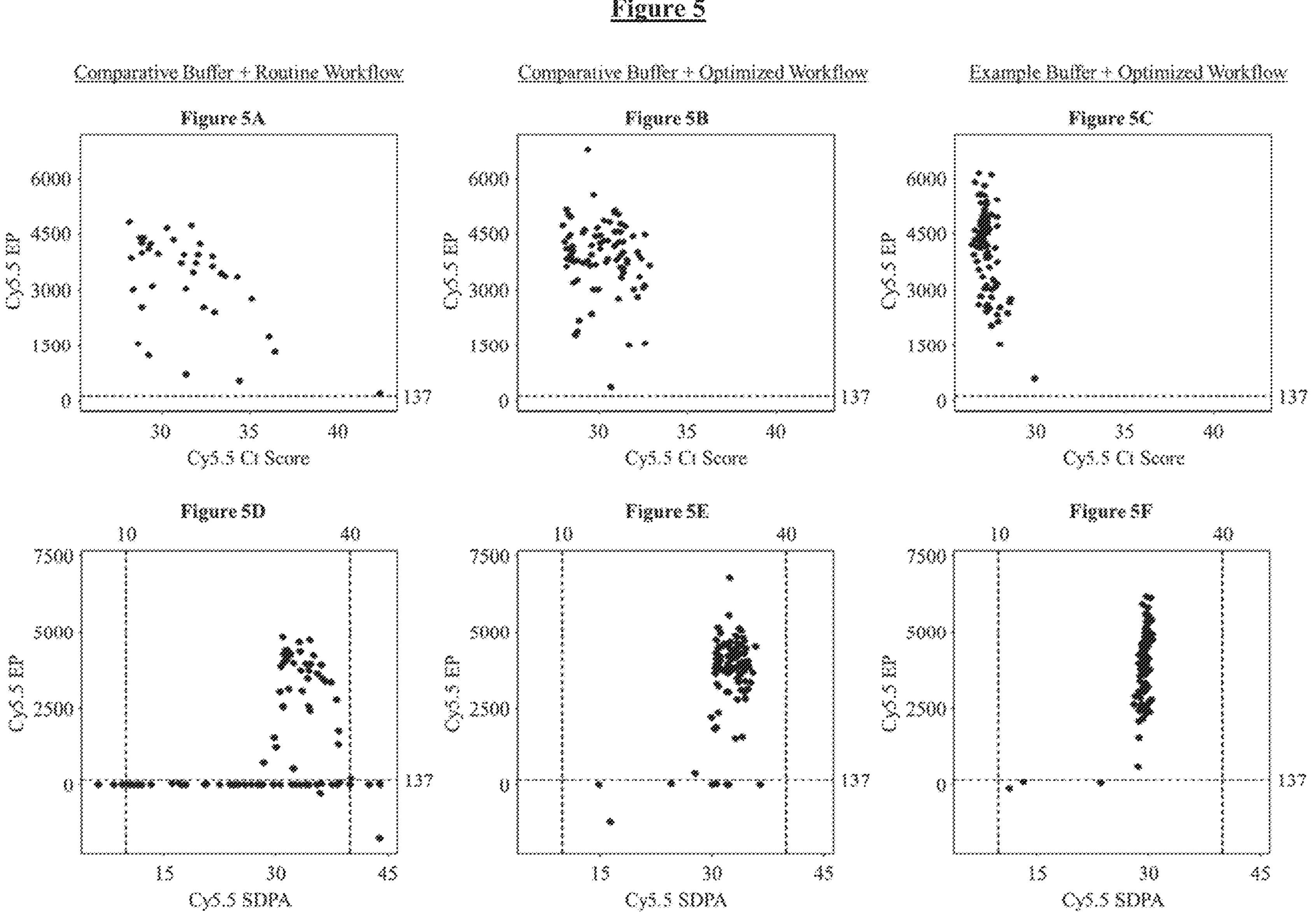
FIGS. 5-6 illustrate embodiments of improved assay performance provided by Example Buffer II, as compared to the Comparative Buffer, in presence of two representative interfering gels: E-Z lubricating jelly (Medline Industries, Inc.) (FIGS. 5A-5F) and non-cabomer-based Surgilube® (FIGS. 6A-6F). Embodiments of assays for detecting bacterial vaginosis (BV) were performed on the BD MAX™ system using either the Comparative Buffer or the Example Buffer. Three sets of scatter plots were generated using the Comparative Buffer following a routine workflow (FIGS. 5A, 5D, 6A, 6D), using the Comparative Buffer following an optimized workflow (FIGS. 5B, 5E, 6B, 6E), and using the Example Buffer following the optimized workflow (FIGS. 5C, 5F, 6C, 6F).
Figures 6, 6A, 6B, 6C, 6D, 6E, 6F:
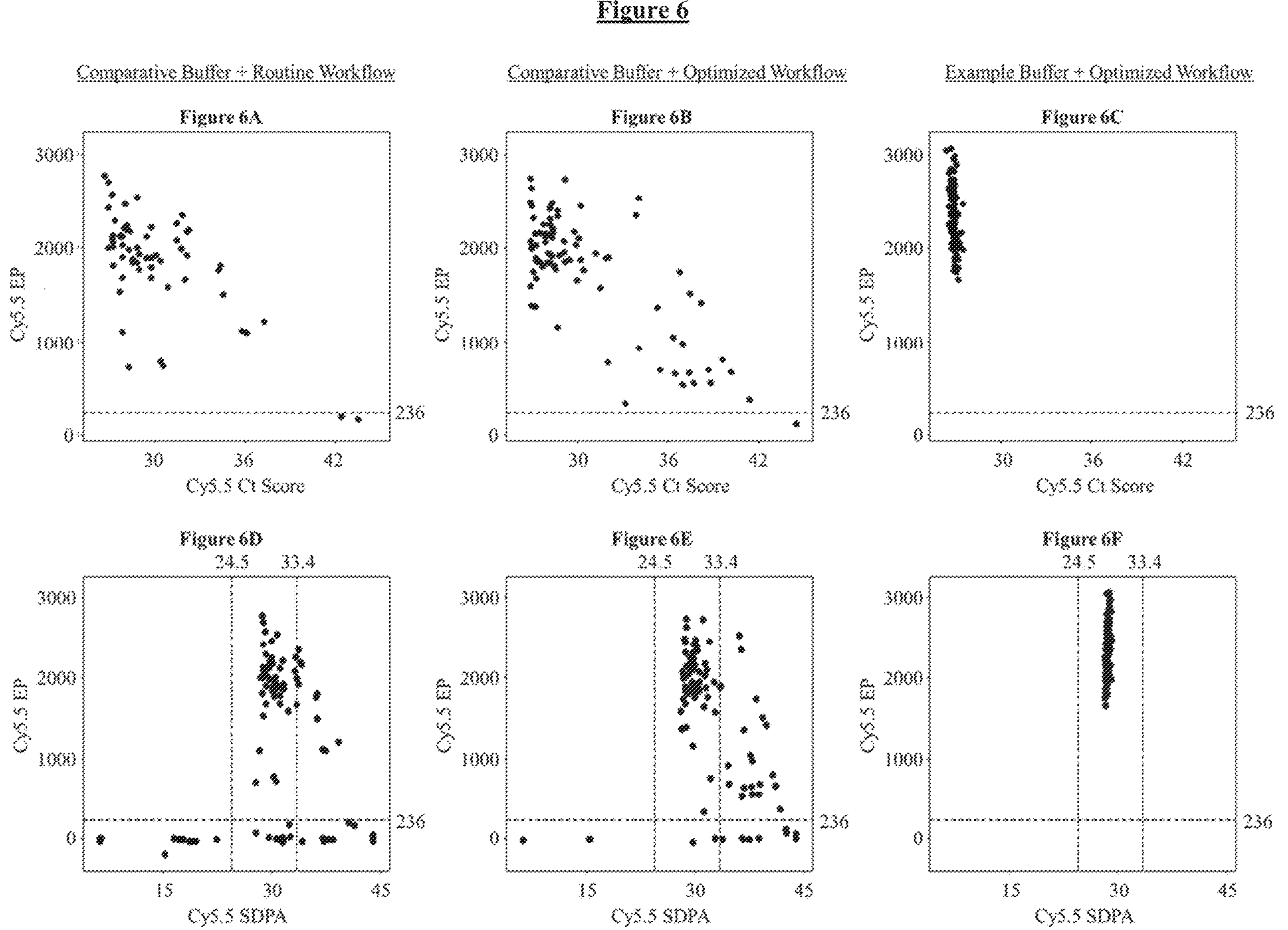

Assays for detecting and diagnosing representative vaginal conditions in samples containing interfering gels were performed on the BD MAX™ system using the Example Buffer II and the Comparative Buffer. The vaginosis testing results in FIG. 5 were obtained from vaginal-swab samples containing interfering E-Z lubricating jelly (Medline Industries, Inc.); and the vaginitis testing results in FIG. 6 from vaginal-swab samples containing interfering Surgilube® lubricant, a gel without carbomers.

Scatter plots were generated from the PCR data obtained, respectively, using the Comparative Buffer following a routine workflow (FIGS. 5A, 5D, 6A, and 6D), using the Comparative Buffer following an optimized workflow (FIGS. 5B, 5E, 6B, and 6E), and using the Example Buffer following the optimized workflow (FIGS. 5C, 5F, 6C, and 6F). The y-axis ("Cy5.5 EP") in FIGS. 5-6 represents the endpoint fluorescence, which measured the fluorescence intensity of Cyanine Dye 5.5 (Cy5.5) at the end of a PCR amplification curve. The x-axis ("Cy5.5 Ct Score"), in FIGS. 5A-5C and 6A-6C, represents the threshold PCR cycle number, at which an amplified product became detectable with confidence, after correction for signal drift. The x-axis ("Cy5.5 SDPA"), in FIGS. 5D-5F and 6D-6F, represents the "second derivative peak abscissa," which was used as criteria for assessing the assay reproducibility. As shown in both FIGS. 5 and 6, the Example Buffer II achieved narrower distributions of the test results in terms of both Ct Score and SDPA than the Comparative Buffer.

As such, this example illustrates that the use of Example Buffer can significantly improve the assay performance, particularly for samples in presence of interfering gels, by improving at least the reproducibility of the diagnostic tests under noise conditions.

Example 10

Example Buffer III Reduces Non-Reportable Rates when Samples Contain Interfering Substances (Lubricants)

An additional study was carried out using a third Example buffer, similar to the study described above for Examples 2 to 9. Example Buffer III contains the following:

| Component | Example Buffer III |
|---|---|
| Acid-base Pair | 10 mM Tris-HCl |
| Surfactant | 1% Triton X-100 |
| Reducing Agent | 15 mM TCEP |
| Monovalent or divalent salt | 50-150 mM $CaCl_2$ |
| pH range | 2.4 ± 0.2 |

As reported with Example Buffers I and II, the use of Example Buffer III reduced the number of indeterminate and unresolved tests compared to a conventional buffer in the presence of an interfering substance (E-Z jelly, Medline Industries, Inc.).

Example 11

Comparison of Example Buffer I to Comparative Buffer BD MAX™ Vaginal Panel and BD MAX™ CT/GC/TV The following example describes the results of a study examining the impact of Buffer I on Non-Reportable Rates (NRR), Percent Agreement and Detection in the BD MAX™ Vaginal Panel assay and the BD MAX™ CT/GC/TV assay. Buffer I was compared to the Comparative Buffer described in Example 1, Table 1.

Laboratory and Clinical Procedures: Samples were collected from donor subjects. For each donor, four collection methods were used:

1) Self-collected vaginal without lubricant
2) Clinician-collected vaginal without lubricant
3) Clinician-collected vaginal with speculum+lubricant (3 different brands)
4) Clinician-collected endocervical with speculum+lubricant (3 different brands)

The lubricants were used on speculum in amounts deemed appropriate by clinician, and three different brands of lubricant were used: Surgilube® surgical lubricant, sterile bacteriostatic (HR® Pharmaceuticals, Inc., York PA), McKesson lubricating jelly (McKesson Medical-Surgical Inc., Richmond VA), Aplicare lubricating jelly (Aplicare, Inc., Meriden CT). Samples were run on the BD MAX™ Vaginal Panel assay and the BD MAX™ CT/GC/TV assay according to manufacturer specifications. The results of the study are shown below.

Table 12 shows that Example Buffer I was very efficient in decreasing NRR (unresolved (UNR) and indeterminate (IND) results) in vaginal samples containing lubricants when run on the BD MAX™ Vaginal Panel (−7.9), although a small increase in NRR (5.5) was observed with the Example I Buffer in vaginal samples collected by clinicians not using lubricants. No significant change was observed in NRR for self-collected vaginal samples or clinician-collected endocervical samples using lubricants.

TABLE 12

Comparison of Example Buffer I (acetate) to Comparative Buffer (phosphate) for BD MAX ™ Vaginal Panel

| Collection | Site | Lubricant | Buffer | UNR | IND | NRR |
|---|---|---|---|---|---|---|
| Self | Vaginal | No | Phosphate | 2.7 | 2.7 | 5.5 |
| | | | Acetate | 3.7 | 2.7 | 6.5 |
| Clinician | Vaginal | No | Phosphate | 1.4 | 2.0 | 3.4 |
| | | | Acetate | 5.1 | 3.8 | 8.9 |
| | | Yes | Phosphate | 7.5 | 4.8 | 12.3 |
| | | | Acetate | 3.0 | 1.4 | 4.4 |
| | Endocervical | Yes | Phosphate | 4.1 | 2.1 | 6.2 |
| | | | Acetate | 4.4 | 2.0 | 6.5 |
| Impact | Self | Vaginal | No | 1.0 | 0.0 | 1.0 |
| Buffer | Clinician | Vaginal | No | 3.8 | 1.7 | 5.5 |
| | | | Yes | −4.5 | −3.4 | −7.9 |
| | | Endocervical | Yes | 0.3 | 0.0 | 0.3 |

As with the BD MAX™ Vaginal Panel, Example I Buffer was efficient in decreasing NRR in vaginal samples containing lubricants when run on the BD MAX™ CT/GC/TV assay (−13.1), but unlike with the BD MAX™ Vaginal Panel, no increase in UNR in vaginal samples collected by clinicians not using lubricants was observed (Table 13). No significant change in NRR for self-collected vaginal samples or clinician-collected endocervical samples using lubricants.

TABLE 13

Comparison of Example Buffer I (acetate) to Comparative Buffer (phosphate) for BD MAX ™ CT/GC/TV

| Collection | Site | Lubricant | Buffer | UNR | IND | NRR |
|---|---|---|---|---|---|---|
| Self | Vaginal | No | Phosphate | 2.1 | 0.0 | 2.1 |
| | | | Acetate | 2.1 | 1.6 | 3.6 |
| Clinician | Vaginal | No | Phosphate | 1.0 | 0.0 | 1.0 |
| | | | Acetate | 1.0 | 0.5 | 1.6 |
| | | Yes | Phosphate | 18.3 | 0.0 | 18.3 |
| | | | Acetate | 3.7 | 1.6 | 5.2 |

TABLE 13-continued

Comparison of Example Buffer I (acetate) to Comparative Buffer (phosphate) for BD MAX ™ CT/GC/TV

| Collection | Site | Lubricant | Buffer | UNR | IND | NRR |
|---|---|---|---|---|---|---|
| | Endocervical | Yes | Phosphate | 1.1 | 0.0 | 1.1 |
| | | | Acetate | 1.1 | 0.5 | 1.6 |
| Impact | Self | Vaginal | No | 0.0 | 1.6 | 1.5 |
| Buffer | Clinician | Vaginal | No | 0.0 | 0.5 | 0.5 |
| | | | Yes | −14.7 | 1.6 | −13.1 |
| | | Endocervical | Yes | 0.0 | 0.5 | 0.5 |

For the BD MAX™ Vaginal Panel assay, Example I Buffer resulted in good agreement with the test results using Comparative Buffer for all targets. Slightly lower positive agreement was observed for *C. glabrata*, but this was due to a very low number of positive results (Table 14).

TABLE 14

Test Result Agreement Between Example Buffer I and Comparative Buffer for BD MAX ™ Vaginal Panel Targets

| Target | Collection | Site | Lubricant | PPA (%) | NPA (%) |
|---|---|---|---|---|---|
| *Candida krusei* | Self | Vaginal | No | 100.0 | 99.6 |
| | Clinician | Vaginal | No | 100.0 | 100.0 |
| | | | Yes | 100.0 | 100.0 |
| | | Endocervical | Yes | 100.0 | 100.0 |
| *T. vaginalis* | Self | Vaginal | No | 100.0 | 99.6 |
| | Clinician | Vaginal | No | 96.7 | 99.6 |
| | | | Yes | 100.0 | 99.6 |
| | | Endocervical | Yes | 100.0 | 99.6 |
| *Candida* group: *C. albicans*, *C. tropicalis*, *C. parapsilosis*, *C. dubliniensis* | Self | Vaginal | No | 91.5 | 95.9 |
| | Clinician | Vaginal | No | 95.2 | 97.0 |
| | | | Yes | 96.7 | 95.4 |
| | | Endocervical | Yes | 92.9 | 97.1 |
| *C. glabrata* | Self | Vaginal | No | 85.7 | 99.6 |
| | Clinician | Vaginal | No | 93.3 | 100.0 |
| | | | Yes | 90.9 | 99.6 |
| | | Endocervical | Yes | 88.9 | 99.6 |
| Bacterial Vaginosis | Self | Vaginal | No | 94.5 | 95.2 |
| | Clinician | Vaginal | No | 92.8 | 96.1 |
| | | | Yes | 97.4 | 95.6 |
| | | Endocervical | Yes | 95.5 | 97.4 |

Legend: PPA % = positive test result percent agreement (number of positive results with the Example Buffer I/number of positive results with comparative buffer); NPA % = negative test result percent agreement (number of negative results with the Example Buffer I/number of negative results with comparative buffer); Bacterial Vaginosis = *Lactobacillus* species (*L. crispatus* and *L. jensenii*), *Gardnerella vaginalis*, *Atopobium vaginae*, Bacterial vaginosis associated bacteria-2 (BVAB-2), Megasphaera-1.

For the BD MAX™ CT/GC/TV assay, Example I Buffer resulted in good agreement with the test results using Comparative Buffer (Table 15).

TABLE 15

Test Result Agreement Between Example Buffer I and Comparative Buffer for BD MAX ™ CT/GC/TV Targets

| Target | Collection | Site | Lubricant | PPA (%) | NPA (%) |
|---|---|---|---|---|---|
| *Chlamydia trachomatis* | Self | Vaginal | No | 100.0 | 100.0 |
| | Clinician | Vaginal | No | 100.0 | 100.0 |
| | | | Yes | 100.0 | 100.0 |
| | | Endocervical | Yes | 100.0 | 100.0 |
| *Neisseria gonorrhoeae* | Self | Vaginal | No | No Data | 100.0 |
| | Clinician | Vaginal | No | No Data | 100.0 |
| | | | Yes | No Data | 100.0 |

TABLE 15-continued

Test Result Agreement Between Example Buffer I and Comparative Buffer for BD MAX ™ CT/GC/TV Targets

| Target | Collection | Site | Lubricant | PPA (%) | NPA (%) |
|---|---|---|---|---|---|
| | | Endocervical | Yes | No Data | 100.0 |
| *Trichomonas vaginalis* | Self | Vaginal | No | 100.0 | 100.0 |
| | Clinician | Vaginal | No | 90.9 | 98.8 |
| | | | Yes | 93.3 | 99.3 |
| | | Endocervical | Yes | 95.2 | 99.4 |

Legend: PPA % = positive test result percent agreement (number of positive results with the Example Buffer I/number of positive results with comparative buffer); NPA % = negative test result percent agreement (number of negative results with the Example Buffer I/number of negative results with comparative buffer).

Based on the analysis of the PCR metrics (EndPoint, SDPA, Ct. score), Example Buffer I tended to slightly negatively impact the amplification of several targets in the BD MAX™ Vaginal Panel assay, while trending toward slightly improving the amplification of TV in the BD MAX™ CT/GC/TV assay.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations can be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above.

Whenever a range of values is provided herein, the range is meant to include the starting value, the ending value, each individual value, or value range there between unless otherwise specifically stated. For example, "from 0.2 to 0.5" means 0.2, 0.3, 0.4, 0.5; ranges there between such as 0.2-0.3, 0.3-0.4, 0.2-0.4; increments there between such as 0.25, 0.35, 0.225, 0.335, 0.49; increment ranges there between such as 0.26-0.39; and the like. As another example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A buffer composition, comprising:

(a) 50 mM to 150 mM acetic acid and 350 mM to 450 mM sodium acetate,
 1 mM to 20 mM ethylenediaminetetraacetic acid (EDTA),
 0.1% w/w to 3% w/w non-ionic surfactant,
 100 mM to 300 mM of a divalent salt selected from the group consisting of calcium salts, magnesium salts, and combinations thereof, and
 a pH of 4.0 to 6.0; or (b) 1 mM to 20 mM Tris-HCl,
 0.1% w/w to 3% w/w non-ionic surfactant,
 1 mM to 30 mM tris(2-carboxyethyl)phosphine (TCEP),
 50 mM to 150 mM of a divalent salt selected from the group consisting of calcium salts, magnesium salts, and combinations thereof, and
 a pH of 2.1 to 3.0.

2. The buffer composition of claim 1, wherein the buffer composition of (a) comprises EDTA at a concentration of about 10 mM or the buffer composition of (b) comprises TCEP at a concentration of about 15 mM.

3. The buffer composition of claim 1, wherein the non-ionic surfactant is selected from the group consisting of ethoxylated non-ionic surfactants, propoxylated non-ionic surfactants, co-ethoxylated-propoxylated non-ionic surfactants, ethoxylated sorbitan esters of mono-fatty acids, ethoxylated octylphenols, ethoxylated secondary C1 to C20 alcohols, co-ethoxylated-propoxylated seed oil alcohols, and combinations thereof.

4. The buffer composition of claim 1, wherein the non-ionic surfactant is selected from the group consisting of ethoxylated sorbitan esters of mono-fatty acids containing an average of 1 to 50 ethylene oxide units per surfactant, ethoxylated octylphenols containing an average of 1 to 20 ethylene oxide units per surfactant, ethoxylated secondary C1 to C20 alcohols containing an average of 1 to 20 ethylene oxide units per surfactant, co-ethoxylated-propoxylated seed oil alcohols containing an average of 1 to 20 propylene oxide units and 1 to 30 ethylene oxide units per surfactant, and combinations thereof.

5. The buffer composition of claim 1, wherein the divalent salt is $CaCl_2$.

6. The buffer composition of claim 1, wherein the buffer composition further comprises a biocidal preservative comprising one or more isothiazolones, wherein the concentration of the biocidal preservative is about 0.01% to about 6% w/w.

7. The buffer composition of claim 6, wherein the biocidal preservative comprises one or more isothiazolones at a concentration of about 0.01% to 1% w/w.

8. The buffer composition of claim 7, wherein the one or more isothiazolones comprise chloromethylisothiazolinone and methylisothiazolinone, and wherein the chloromethylisothiazolinone and methylisothiazolinone are present at a weight ratio from about 1:1 to about 5:1.

9. The buffer composition of claim 8, wherein the one or more isothiazolones comprise 5-chloro-2-methyl-4-isothiazolin-3-one and 2-methyl-4-isothiazolin-3-one at a weight ratio of about 3:1.

10. The buffer composition of claim 1, wherein the buffer composition further comprises a biocidal preservative, wherein the biocidal preservative comprises one or more of a salt-free glycol and an alkyl carboxylate stabilizer.

11. The buffer composition of claim 1, wherein the buffer composition of (b) comprises 10 mM to 20 mM TCEP.

12. The buffer composition of claim 11, wherein the divalent salt of buffer composition of (b) is $CaCl_2$.

13. A kit for diagnosing a condition associated with vaginal infections or inflammation, the kit comprising:

the buffer composition of claim 1, and reagents for PCR detection of microbiome organisms associated with vaginal infections or inflammation.

14. A buffer composition comprising:

10 mM Tris-HCl,

1% polyethylene glycol p-(1,1,3,3-tetramethylbutyl)-phenyl ether, 15 mM TCEP, 50-150 mM $CaCl_2$, and a pH of 2.4±0.2.

15. A kit for diagnosing a condition associated with vaginal infections or inflammation, the kit comprising:

the buffer composition of claim 14, and reagents for PCR detection of microbiome organisms associated with vaginal infections or inflammation.

16. A buffer composition comprising:

50 mM to 150 mM acetic acid, 350 mM to 450 mM sodium acetate, 1 mM to 20 mM EDTA, 0.1% w/w to 3% w/w non-ionic surfactant, 100 mM to 300 mM $CaCl_2$, 0.01% to 1% chloromethylisothiazolinone and methylisothiazolinone, and a pH of 4.0 to 6.0.

17. The buffer composition of claim 16, wherein the surfactant comprises 1% w/w non-ionic secondary alcohol ethoxylate or 0.5% w/w polyethylene glycol p-(1,1,3,3-tetramethylbutyl)-phenyl ether.

18. A kit for diagnosing a condition associated with vaginal infections or inflammation, the kit comprising:

the buffer composition of claim 16, and reagents for PCR detection of microbiome organisms associated with vaginal infections or inflammation.

* * * * *